United States Patent
Thompson et al.

(10) Patent No.: US 11,931,112 B2
(45) Date of Patent: Mar. 19, 2024

(54) SHAPE-SENSING SYSTEM AND METHODS FOR MEDICAL DEVICES

(71) Applicant: Bard Access Systems, Inc., Salt Lake City, UT (US)

(72) Inventors: Chase Thompson, Bountiful, UT (US); Shayne Messerly, Kaysville, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 686 days.

(21) Appl. No.: 16/984,104

(22) Filed: Aug. 3, 2020

(65) Prior Publication Data

US 2021/0045814 A1 Feb. 18, 2021

Related U.S. Application Data

(60) Provisional application No. 62/885,702, filed on Aug. 12, 2019.

(51) Int. Cl.
*A61B 34/20* (2016.01)
*A61B 46/23* (2016.01)
(Continued)

(52) U.S. Cl.
CPC .............. *A61B 34/20* (2016.02); *A61B 46/23* (2016.02); *A61M 25/0097* (2013.01);
(Continued)

(58) Field of Classification Search
CPC .................... A61B 34/20; A61B 46/23; A61B 2017/00044; A61B 2017/00199;
(Continued)

(56) References Cited

U.S. PATENT DOCUMENTS 4,813,429 A 3/1989 Eshel et al.
5,099,845 A 3/1992 Besz et al.
(Continued)

FOREIGN PATENT DOCUMENTS

DE 102016109601 A1 11/2017
EP 2240111 A2 10/2010
(Continued)

OTHER PUBLICATIONS

PCT/US2021/019713 filed Feb. 25, 2021 International Search Report and Written Opinion dated Jul. 6, 2021.
(Continued)

*Primary Examiner* — Baisakhi Roy
*Assistant Examiner* — Kaitlyn E Sebastian
(74) *Attorney, Agent, or Firm* — Rutan & Tucker LLP

(57) ABSTRACT

Shape-sensing systems and methods for medical devices. The shape-sensing system can include a medical device, an optical interrogator, a console, and a display screen. The medical device can include an integrated optical-fiber stylet having fiber Bragg grating ("FBG") sensors along at least a distal-end portion thereof. The optical interrogator can be configured to send input optical signals into the optical-fiber stylet and receive FBG sensor-reflected optical signals therefrom. The console can be configured to convert the reflected optical signals into plottable data for displaying plots thereof on the display screen. The plots can include a plot of curvature vs. time for each FBG sensor of a selection of the FBG sensors in the distal-end portion of the optical-fiber stylet for identifying a distinctive change in strain of the optical-fiber stylet as a tip of the medical device is advanced into a superior vena cava of a patient.

36 Claims, 15 Drawing Sheets

(51) Int. Cl.
*A61M 25/00* (2006.01)
*A61M 25/01* (2006.01)
*A61M 25/09* (2006.01)
*A61B 17/00* (2006.01)

(52) U.S. Cl.
CPC ........ *A61M 25/0102* (2013.01); *A61M 25/09* (2013.01); *A61B 2017/00044* (2013.01); *A61B 2017/00199* (2013.01); *A61B 2034/2061* (2016.02); *A61B 2046/234* (2016.02); *A61B 2562/0219* (2013.01); *A61B 2562/0223* (2013.01)

(58) Field of Classification Search
CPC ...... A61B 2034/2061; A61B 2046/234; A61B 2562/0219; A61B 2562/0223; A61B 2034/2048; A61B 2034/2055; A61M 25/0097; A61M 25/0102; A61M 25/09; A61M 25/0105
See application file for complete search history.

(56) References Cited

U.S. PATENT DOCUMENTS

| | | | |
|---|---|---|---|
| 5,163,935 A | 11/1992 | Black et al. | |
| 5,207,672 A | 5/1993 | Roth et al. | |
| 5,211,165 A | 5/1993 | Dumoulin et al. | |
| 5,275,151 A | 1/1994 | Shockey et al. | |
| 5,280,786 A | 1/1994 | Wlodarczyk et al. | |
| 5,423,321 A | 6/1995 | Fontenot | |
| 5,454,807 A | 10/1995 | Lennox et al. | |
| 5,517,997 A | 5/1996 | Fontenot | |
| 5,622,170 A | 4/1997 | Schulz | |
| 5,740,808 A | 4/1998 | Panescu et al. | |
| 5,872,879 A | 2/1999 | Hamm | |
| 5,873,842 A | 2/1999 | Brennen et al. | |
| 5,879,306 A | 3/1999 | Fontenot et al. | |
| 5,906,579 A | 5/1999 | Vander Salm et al. | |
| 6,069,698 A | 5/2000 | Ozawa et al. | |
| 6,081,741 A | 6/2000 | Hollis | |
| 6,178,346 B1 | 1/2001 | Amundson et al. | |
| 6,208,887 B1 | 3/2001 | Clarke | |
| 6,319,227 B1 | 11/2001 | Mansouri-Ruiz | |
| 6,343,227 B1 | 1/2002 | Crowley | |
| 6,398,721 B1 | 6/2002 | Nakamura et al. | |
| 6,485,482 B1 | 11/2002 | Belef | |
| 6,564,089 B2 | 5/2003 | Izatt et al. | |
| 6,593,884 B1 | 7/2003 | Gilboa et al. | |
| 6,597,941 B2 | 7/2003 | Fontenot et al. | |
| 6,650,923 B1 | 11/2003 | Lesh et al. | |
| 6,685,666 B1 | 2/2004 | Fontenot | |
| 6,687,010 B1 | 2/2004 | Horii et al. | |
| 6,690,966 B1 | 2/2004 | Rava et al. | |
| 6,701,181 B2 | 3/2004 | Tang et al. | |
| 6,711,426 B2 | 3/2004 | Benaron et al. | |
| 6,816,743 B2 | 11/2004 | Moreno et al. | |
| 6,892,090 B2 | 5/2005 | Verard et al. | |
| 6,895,267 B2 | 5/2005 | Panescu et al. | |
| 7,132,645 B2 | 11/2006 | Korn | |
| 7,273,056 B2 | 9/2007 | Wilson et al. | |
| 7,344,533 B2 | 3/2008 | Pearson et al. | |
| 7,366,562 B2 | 4/2008 | Dukesherer et al. | |
| 7,366,563 B2 | 4/2008 | Kleen et al. | |
| 7,396,354 B2 | 7/2008 | Rychnovsky et al. | |
| 7,406,346 B2 | 7/2008 | Kleen et al. | |
| 7,515,265 B2 | 4/2009 | Alfano et al. | |
| 7,532,920 B1 | 5/2009 | Ainsworth et al. | |
| 7,587,236 B2 | 9/2009 | Demos et al. | |
| 7,603,166 B2 | 10/2009 | Casscells, III et al. | |
| 7,729,735 B1 | 6/2010 | Burchman | |
| 7,757,695 B2 | 7/2010 | Wilson et al. | |
| 7,758,499 B2 | 7/2010 | Adler | |
| 7,840,253 B2 | 11/2010 | Tremblay et al. | |
| 7,992,573 B2 | 8/2011 | Wilson et al. | |
| 8,032,200 B2 | 10/2011 | Tearney et al. | |
| 8,054,469 B2 | 11/2011 | Nakabayashi et al. | |
| 8,060,187 B2 | 11/2011 | Marshik-Geurts et al. | |
| 8,073,517 B1 | 12/2011 | Burchman | |
| 8,078,261 B2 | 12/2011 | Imam | |
| 8,187,189 B2 | 5/2012 | Jung et al. | |
| 8,267,932 B2 | 9/2012 | Baxter et al. | |
| 8,369,932 B2 | 2/2013 | Cinbis et al. | |
| 8,388,541 B2 | 3/2013 | Messerly et al. | |
| 8,571,640 B2 | 10/2013 | Holman | |
| 8,597,315 B2 | 12/2013 | Snow et al. | |
| 8,700,358 B1 | 4/2014 | Parker, Jr. | |
| 8,781,555 B2 | 7/2014 | Burnside et al. | |
| 8,798,721 B2 | 8/2014 | Dib | |
| 8,968,331 B1 | 3/2015 | Sochor | |
| 8,979,871 B2 | 3/2015 | Tyc et al. | |
| 9,060,687 B2 | 6/2015 | Yamanaka et al. | |
| 9,360,630 B2 | 6/2016 | Jenner et al. | |
| 9,504,392 B2 | 11/2016 | Caron et al. | |
| 9,560,954 B2 | 2/2017 | Jacobs et al. | |
| 9,622,706 B2 | 4/2017 | Dick et al. | |
| 9,678,275 B1 | 6/2017 | Griffin | |
| 10,231,753 B2 | 3/2019 | Burnside et al. | |
| 10,327,830 B2 | 6/2019 | Grant et al. | |
| 10,349,890 B2 | 7/2019 | Misener et al. | |
| 10,492,876 B2 | 12/2019 | Anastassiou et al. | |
| 10,568,586 B2 | 2/2020 | Begin et al. | |
| 10,631,718 B2 | 4/2020 | Petroff et al. | |
| 10,992,078 B2 | 4/2021 | Thompson et al. | |
| 11,123,047 B2 | 9/2021 | Jaffer et al. | |
| 2002/0198457 A1 | 12/2002 | Tearney et al. | |
| 2003/0092995 A1 | 5/2003 | Thompson | |
| 2004/0242995 A1 | 12/2004 | Maschke | |
| 2005/0033264 A1 | 2/2005 | Redinger | |
| 2005/0261598 A1 | 11/2005 | Banet et al. | |
| 2006/0013523 A1 | 1/2006 | Childers et al. | |
| 2006/0036164 A1 | 2/2006 | Wilson et al. | |
| 2006/0189959 A1 | 8/2006 | Schneiter | |
| 2006/0200049 A1 | 9/2006 | Leo et al. | |
| 2006/0241395 A1 | 10/2006 | Kruger et al. | |
| 2006/0241492 A1 | 10/2006 | Boese et al. | |
| 2007/0156019 A1 | 7/2007 | Larkin et al. | |
| 2007/0201793 A1 | 8/2007 | Askins et al. | |
| 2007/0287886 A1 | 12/2007 | Saadat | |
| 2007/0299425 A1 | 12/2007 | Waner et al. | |
| 2008/0039715 A1 | 2/2008 | Wilson et al. | |
| 2008/0082004 A1 | 4/2008 | Banet et al. | |
| 2008/0172119 A1 | 7/2008 | Yamasaki et al. | |
| 2008/0183128 A1 | 7/2008 | Morriss et al. | |
| 2008/0285909 A1 | 11/2008 | Younge et al. | |
| 2009/0054908 A1 | 2/2009 | Zand et al. | |
| 2009/0062634 A1 | 3/2009 | Say et al. | |
| 2009/0137952 A1* | 5/2009 | Ramamurthy | A61B 5/06 604/95.01 |
| 2009/0234328 A1 | 9/2009 | Cox et al. | |
| 2009/0304582 A1 | 12/2009 | Rousso et al. | |
| 2009/0314925 A1 | 12/2009 | Van Vorhis et al. | |
| 2010/0016729 A1 | 1/2010 | Futrell | |
| 2010/0030063 A1 | 2/2010 | Lee et al. | |
| 2010/0114115 A1 | 5/2010 | Schlesinger et al. | |
| 2010/0286531 A1 | 11/2010 | Ryan et al. | |
| 2010/0312095 A1 | 12/2010 | Jenkins et al. | |
| 2011/0144481 A1 | 6/2011 | Feer et al. | |
| 2011/0166442 A1 | 7/2011 | Sarvazyan | |
| 2011/0172680 A1 | 7/2011 | Younge et al. | |
| 2011/0237958 A1 | 9/2011 | Onimura | |
| 2011/0245662 A1 | 10/2011 | Eggers et al. | |
| 2011/0295108 A1 | 12/2011 | Cox et al. | |
| 2011/0313280 A1 | 12/2011 | Govari et al. | |
| 2012/0046562 A1 | 2/2012 | Powers et al. | |
| 2012/0101413 A1 | 4/2012 | Beetel et al. | |
| 2012/0136242 A1 | 5/2012 | Qi et al. | |
| 2012/0143029 A1 | 6/2012 | Silverstein et al. | |
| 2012/0184827 A1 | 7/2012 | Shwartz et al. | |
| 2012/0184955 A1 | 7/2012 | Pivotto et al. | |
| 2012/0321243 A1 | 12/2012 | Younge et al. | |
| 2013/0028554 A1 | 1/2013 | Wong et al. | |
| 2013/0096482 A1 | 4/2013 | Bertrand et al. | |
| 2013/0104884 A1 | 5/2013 | Vazales et al. | |
| 2013/0188855 A1 | 7/2013 | Desjardins et al. | |

(56) References Cited

U.S. PATENT DOCUMENTS

| | | |
|---|---|---|
| 2013/0204124 A1 | 8/2013 | Duindam et al. |
| 2013/0211246 A1 | 8/2013 | Parasher |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0121468 A1 | 5/2014 | Eichenholz |
| 2014/0221829 A1 | 8/2014 | Maitland et al. |
| 2014/0275997 A1 | 9/2014 | Chopra et al. |
| 2015/0029511 A1 | 1/2015 | Hooft et al. |
| 2015/0031987 A1* | 1/2015 | Pameijer ............ A61M 25/0105 600/424 |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0190221 A1 | 7/2015 | Schaefer et al. |
| 2015/0209113 A1 | 7/2015 | Burkholz et al. |
| 2015/0209117 A1 | 7/2015 | Flexman et al. |
| 2015/0254526 A1 | 9/2015 | Denissen |
| 2015/0320977 A1 | 11/2015 | Vitullo et al. |
| 2016/0018602 A1 | 1/2016 | Govari et al. |
| 2016/0166326 A1 | 6/2016 | Bakker et al. |
| 2016/0166341 A1* | 6/2016 | Iordachita ............ G01B 11/165 250/227.14 |
| 2016/0184020 A1 | 6/2016 | Kowalewski et al. |
| 2016/0213432 A1 | 7/2016 | Flexman et al. |
| 2016/0354038 A1 | 12/2016 | Demirtas et al. |
| 2017/0020394 A1 | 1/2017 | Harrington |
| 2017/0079681 A1 | 3/2017 | Burnside et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1* | 8/2017 | Flexman ............ G01D 5/35358 |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0311901 A1 | 11/2017 | Zhao et al. |
| 2017/0319279 A1 | 11/2017 | Fish et al. |
| 2018/0095231 A1 | 4/2018 | Lowell et al. |
| 2018/0113038 A1 | 4/2018 | Janabi-Sharifi et al. |
| 2018/0140170 A1 | 5/2018 | Van Putten et al. |
| 2018/0235709 A1 | 8/2018 | Donhowe et al. |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0279909 A1 | 10/2018 | Noonan et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2019/0059743 A1 | 2/2019 | Ramachandran et al. |
| 2019/0110844 A1 | 4/2019 | Misener et al. |
| 2019/0231272 A1 | 8/2019 | Yamaji |
| 2019/0237902 A1 | 8/2019 | Thompson et al. |
| 2019/0307331 A1 | 10/2019 | Saadat et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374130 A1 | 12/2019 | Bydlon et al. |
| 2020/0046434 A1 | 2/2020 | Graetzel et al. |
| 2020/0054399 A1 | 2/2020 | Duindam et al. |
| 2020/0305983 A1 | 10/2020 | Yampolsky et al. |
| 2020/0315770 A1 | 10/2020 | Dupont et al. |
| 2021/0023341 A1 | 1/2021 | Decheek et al. |
| 2021/0068911 A1 | 3/2021 | Walker et al. |
| 2021/0298680 A1 | 3/2021 | Sowards et al. |
| 2021/0244311 A1 | 8/2021 | Zhao et al. |
| 2021/0268229 A1 | 9/2021 | Sowards et al. |
| 2021/0271035 A1 | 9/2021 | Sowards et al. |
| 2021/0275257 A1 | 9/2021 | Prior et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0011192 A1 | 1/2022 | Misener et al. |
| 2022/0034733 A1 | 2/2022 | Misener et al. |
| 2022/0096796 A1 | 3/2022 | McLaughlin et al. |
| 2022/0110695 A1 | 4/2022 | Sowards et al. |
| 2022/0152349 A1 | 5/2022 | Sowards et al. |
| 2022/0160209 A1 | 5/2022 | Sowards et al. |
| 2022/0172354 A1 | 6/2022 | Misener et al. |
| 2022/0211442 A1 | 7/2022 | McLaughlin et al. |
| 2022/0233246 A1 | 7/2022 | Misener et al. |
| 2022/0369934 A1 | 11/2022 | Sowards et al. |
| 2023/0081198 A1 | 3/2023 | Sowards et al. |
| 2023/0097431 A1 | 3/2023 | Sowards et al. |
| 2023/0101030 A1 | 3/2023 | Misener et al. |
| 2023/0108604 A1 | 4/2023 | Messerly et al. |
| 2023/0126813 A1 | 4/2023 | Sowards et al. |
| 2023/0243715 A1 | 8/2023 | Misener et al. |
| 2023/0248444 A1 | 8/2023 | Misener et al. |
| 2023/0251150 A1 | 8/2023 | Misener et al. |
| 2023/0337985 A1 | 10/2023 | Sowards et al. |

FOREIGN PATENT DOCUMENTS

| | | |
|---|---|---|
| EP | 3545849 A1 | 10/2019 |
| EP | 3705020 A1 | 9/2020 |
| KR | 20190098512 A | 8/2019 |
| WO | 99/64099 A1 | 12/1999 |
| WO | 1999064099 A1 | 12/1999 |
| WO | 2006122001 A2 | 11/2006 |
| WO | 2009/155325 A2 | 12/2009 |
| WO | 2011121516 A2 | 10/2011 |
| WO | 2011141830 A1 | 11/2011 |
| WO | 2011150376 A1 | 12/2011 |
| WO | 2012064769 A2 | 5/2012 |
| WO | 2015044930 A1 | 4/2015 |
| WO | 2015074045 A2 | 5/2015 |
| WO | 2016038492 A1 | 3/2016 |
| WO | 2016/061431 A1 | 4/2016 |
| WO | 2016051302 A1 | 4/2016 |
| WO | 2018/096491 A1 | 5/2018 |
| WO | 2019037071 A1 | 2/2019 |
| WO | 2019/046769 A1 | 3/2019 |
| WO | 2019070423 A1 | 4/2019 |
| WO | 2019230713 A1 | 12/2019 |
| WO | 2020/182997 A1 | 9/2020 |
| WO | 2021030092 A1 | 2/2021 |
| WO | 2021108688 A1 | 6/2021 |
| WO | 2021108697 A1 | 6/2021 |
| WO | 2021/138096 A1 | 7/2021 |
| WO | 2021216089 A1 | 10/2021 |
| WO | 2022/031613 A1 | 2/2022 |
| WO | 2022/081723 A1 | 4/2022 |
| WO | 2022150411 A1 | 7/2022 |
| WO | 2022/164902 A1 | 8/2022 |
| WO | 2022/245987 A1 | 11/2022 |
| WO | 2023043954 A1 | 3/2023 |
| WO | 2023049443 A1 | 3/2023 |
| WO | 2023/055810 A1 | 4/2023 |
| WO | 2023/076143 A1 | 5/2023 |

OTHER PUBLICATIONS

PCT/US2021/020079 filed Feb. 26, 2021 International Search Report and Written Opinion dated Jun. 4, 2021.

U.S. Appl. No. 15/947,267, filed Apr. 6, 2018 Final Office Action dated Jun. 30, 2021.

U.S. Appl. No. 15/947,267, filed Apr. 6, 2018 Non-Final Office Action dated Mar. 12, 2021.

Fiber Optic RealShape (FORS) technology—research. Philips. (Oct. 18, 2018). Retrieved Feb. 28, 2023, from https:// www.philips.com/a-w/research/research-programs/fors.html (Year: 2018).

U.S. Appl. No. 17/105,310, filed Nov. 25, 2020 Non-Final Office Action dated Feb. 22, 2023.

U.S. Appl. No. 17/357,186, filed Jun. 24, 2021 Restriction Requirement dated Mar. 7, 2023.

U.S. Appl. No. 17/392,002, filed Aug. 2, 2021, Corrected Notice of Allowability dated Feb. 23, 2023.

U.S. Appl. No. 17/500,678, filed Oct. 13, 2021 Non-Final Office Action dated Mar. 15, 2023.

(56) References Cited

OTHER PUBLICATIONS

Jackle Sonja et al. "Three-dimensional guidance including shape sensing of a stentgraft system for endovascular aneurysm repair." International Journal of Computer Assisted Radiology and Surgery, Springer DE. vol. 15, No. 6, May 7, 2020.
PCT/US2022/029894 filed May 18, 2022, International Search Report and Written Opinion dated Sep. 1, 2022.
PCT/US2022/043706 filed Sep. 16, 2022 International Search Report and Written Opinion dated Nov. 24, 2022.
PCT/US2022/044696 filed Sep. 26, 2022 International Search Report and Written Opinion dated Jan. 23, 2023.
PCT/US2022/045051 filed Sep. 28, 2022 International Search Report and Written Opinion dated Jan. 2, 2023.
PCT/US2022/047538 filed Oct. 24, 2022 International Search Report and Written Opinion dated Jan. 26, 2023.
U.S. Appl. No. 15/947,267, filed Apr. 6, 2018 Examiner's Answer dated Nov. 28, 2022.
U.S. Appl. No. 17/357,561, filed Jun. 24, 2021 Non-Final Office Action dated Aug. 11, 2022.
U.S. Appl. No. 17/357,561, filed Jun. 24, 2021 Notice of Allowance dated Dec. 9, 2022.
U.S. Appl. No. 17/371,993, filed Jul. 9, 2021 Notice of Allowance dated Nov. 3, 2022.
U.S. Appl. No. 17/392,002, filed Aug. 2, 2021, Non-Final Office Action dated Sep. 12, 2022.
U.S. Appl. No. 17/392,002, filed Aug. 2, 2021, Notice of Allowance dated Jan. 19, 2023.
PCT/US2018/026493 filed Apr. 6, 2018 International Search Report and Written Opinion dated Jun. 22, 2018.
U.S. Appl. No. 15/947,267, filed Apr. 6, 2018 Non-Final Office Action dated May 29, 2020.
PCT/US2021 /059755 filed Nov. 17, 2021 International Search Report and Written Opinion dated Apr. 29, 2022.
PCT/US2021/054802 filed Oct. 13, 2021 International Search Report and Written Opinion dated Feb. 2, 2022.
PCT/US2021/060849 filed Nov. 24, 2021 International Search Report and Written Opinion dated Mar. 9, 2022.
U.S. Appl. No. 15/947,267, filed Apr. 6, 2018 Final Office Action dated Apr. 22, 2022.
PCT/US2020/062396 filed Nov. 25, 2020 International Preliminary Report on Patentability dated Jan. 29, 2021.
PCT/US2020/062407 filed Nov. 25, 2020 International Preliminary Report on Patentability dated Jan. 25, 2021.
PCT/US2022/011347 filed Jan. 5, 2022 International Search Report and Written Opinion dated May 3, 2022.
PCT/US2022/013897 filed Jan. 26, 2022 International Search Report and Written Opinion dated May 11, 2022.
U.S. Appl. No. 17/105,259, filed Nov. 25, 2020, Notice of Allowance dated Jul. 20, 2022.
U.S. Appl. No. 17/371,993, filed Jul. 9, 2021 Non-Final Office Action dated Jul. 12, 2022.
PCT/US2020/062396 filed Nov. 25, 2020 International Search Report and Written Opinion dated Mar. 2, 2021.
PCT/US2020/062407 filed Nov. 25, 2020 International Search Report and Written Opinion dated Mar. 11, 2021.
PCT/US2021/020732 filed Mar. 3, 2021 International Search Report and Written Opinion dated Jul. 5, 2021.
U.S. Appl. No. 15/947,267, filed Apr. 6, 2018 Non-Final Office Action dated Oct. 13, 2021.
PCT/US2020/044801 filed Aug. 3, 2020 International Search Report and Written Opinion dated Oct. 26, 2020.
U.S. Appl. No. 15/947,267, filed Apr. 6, 2018 Final Office Action dated Nov. 10, 2020.
PCT/US2021/038899 filed Jun. 24, 2021 International Search Report and Written Opinion dated Oct. 6, 2021.
PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
PCT/US2021/044216 filed Aug. 2, 2021 International Search Report and Written Opinion dated Nov. 18, 2021.
U.S. Appl. No. 17/185,777, filed Feb. 25, 2021 Non-Final Office Action dated Feb. 9, 2022.
EP 20853352.1 filed Mar. 7, 2022 Extended European Search Report dated Jul. 27, 2023.
PCT/US2023/019239 filed Apr. 20, 2023 International Search Report and Written Opinion dated Jul. 20, 2023.
U.S. Appl. No. 17/105,310, filed Nov. 25, 2020 Notice of Allowance dated Aug. 2, 2023.
U.S. Appl. No. 17/357,186, filed Jun. 24, 2021 Non Final Office Action dated May 30, 2023.
U.S. Appl. No. 17/357,186, filed Jun. 24, 2021 Notice of Allowance dated Aug. 23, 2023.
Dziuda L et al: "Monitoring Respiration and Cardiac Activity Using Fiber Bragg Grating-Based Sensor", IEEE Transactions on Biomedical Engineering vol. 59, No. 7, Jul. 2012 pp. 1934-1942.
Dziuda L. et al: "Fiber-optic sensor for monitoring respiration and cardiac activity", 2011 IEEE Sensors Proceedings : Limerick, Ireland, Oct. 2011 pp. 413-416.
EP 20893677.3 filed Jun. 22, 2022 Extended European Search Report dated Oct. 13, 2023.
EP 20894633.5 filed Jun. 22, 2022 Extended European Search Report dated Oct. 16, 2023.
PCT/US2023/026487 filed Jun. 28, 2023 International Search Report and Written Opinion dated Sep. 6, 2023.
PCT/US2023/026581 filed Jun. 29, 2023 International Search Report and Written Opinion dated Oct. 27, 2023.
U.S. Appl. No. 17/484,960, filed Sep. 24, 2021 Non-Final Office Action dated Oct. 5, 2023.
U.S. Appl. No. 17/500,678, filed Oct. 13, 2021 Final Office Action dated Sep. 21, 2023.

* cited by examiner

SHAPE-SENSING SYSTEM AND METHODS FOR MEDICAL DEVICES

PRIORITY

This application claims the benefit of priority to U.S. Provisional Application No. 62/885,702, filed Aug. 12, 2019, which is incorporated by reference in its entirety into this application.

BACKGROUND

At times, a tip of a peripherally inserted central catheter ("PICC") or central venous catheter ("CVC") can move becoming displaced from an ideal position in a patient's superior vena cava ("SVC"). A clinician believing such a PICC or CVC has displaced typically checks for displacement by chest X-ray and replaces the PICC or CVC if necessary. However, X-rays expose patients to ionizing radiation. Therefore, there is a need for clinicians to easily and safely check for displacement of PICCs and CVCs for replacement thereof if necessary.

Disclosed herein are shape-sensing systems and methods for medical devices that address the foregoing.

SUMMARY

Disclosed herein is a shape-sensing system for medical devices including, in some embodiments, a medical device, an optical interrogator, a console, and a display screen. The medical device includes a body of implementation including an optical fiber, wherein the optical fiber is comprised of a number of fiber Bragg grating ("FBG") sensors along at least a distal-end portion of the optical-fiber. One embodiment of the body of implementation, as will be discussed primarily throughout the disclosure, is an optical-fiber integrated stylet. However, other embodiments of body of implementation include, but are not limited to, an integrated optical-fiber guidewire, or an integrated optical-fiber catheter. The optical interrogator is configured to send input optical signals into the optical-fiber stylet and receive FBG sensor-reflected optical signals from the optical-fiber stylet. The console includes memory and one or more processors configured to convert the FBG sensor-reflected optical signals from the optical-fiber stylet into plottable data by way of a number of optical signal-converter logic, which may include one or more algorithms. The display screen is configured for displaying any plot of a number of plots of the plottable data. The number of plots include at least a plot of curvature vs. time for each FBG sensor of a selection of the FBG sensors in the distal-end portion of the optical-fiber stylet for identifying a distinctive change in strain of the optical-fiber stylet at a moment a tip of the medical device is advanced into an SVC of a patient.

In some embodiments, the shape-sensing system further includes an SVC-determiner algorithm configured to automatically determine the distinctive change in the strain of the optical-fiber stylet at the moment the tip of the medical device is advanced into the SVC of the patient. The distinctive change in the strain is an instantaneous increase in the strain followed by an instantaneous decrease in the strain.

In some embodiments, the SVC-determiner algorithm is configured to confirm the tip of the medical device is in the SVC by way of periodic changes in the strain of the optical-fiber stylet sensed by the selection of the FBG sensors. The periodic changes in the strain result from periodic changes in blood flow within the SVC as a heart of the patient beats.

In some embodiments, the shape-sensing system further includes an optical-fiber connector module configured to establish a first optical connection from the medical device to the optical-fiber connection module and a second optical connection from the optical-fiber connection module to the optical interrogator. The first optical connection is through a sterile drape with the medical device in a sterile field defined by the sterile drape and the optical-fiber connector module in a non-sterile field defined by the sterile drape.

In some embodiments, the optical-fiber connector module includes one or more sensors selected from a gyroscope, an accelerometer, and a magnetometer. The one or more sensors are configured to provide sensor data to the console over one or more data wires for algorithmically determining a reference plane for shape sensing with the optical-fiber stylet.

In some embodiments, the optical interrogator is an integrated optical interrogator integrated into the console.

In some embodiments, the display screen is an integrated display screen integrated into the console.

Also disclosed herein is a method for determining a tip of a medical device is located within an SVC of a patient. The method includes, in some embodiments, advancing the tip of the medical device through a vasculature of the patient toward the SVC. The medical device includes an integrated optical-fiber stylet having a number of FBG sensors along at least a distal-end portion of the optical-fiber stylet for shape sensing with a shape-sensing system including the medical device. The method also includes enabling input optical signals (e.g., broadband incident light) to be sent into the optical-fiber stylet while advancing the tip of the medical device through the vasculature of the patient. In one embodiment, the broadband incident light is provided by a light source which may be a tunable swept laser, although other suitable light sources can also be employed in addition to a laser, including semi-coherent light sources, LED light sources, etc. The method also includes enabling FBG sensor-reflected optical signals to be received from the optical-fiber stylet while advancing the tip of the medical device through the vasculature of the patient. The method also includes identifying on a display screen of the shape-sensing system a distinctive change in strain of the optical-fiber stylet sensed by a selection of the FBG sensors in the distal-end portion of the optical-fiber stylet at a moment the tip of the medical device is advanced into the SVC, thereby determining the tip of the medical device is located within the SVC.

In some embodiments, the method further includes enabling the FBG sensor-reflected optical signals received from the optical-fiber stylet to be algorithmically converted into a number of different plots for display on the display screen.

In some embodiments, each plot of the number of different plots is selected from a plot of curvature vs. arc length, a plot of torsion vs. arc length, a plot of angle vs. arc length, and a plot of position vs. time for at least the distal-end portion of the optical-fiber stylet.

In some embodiments, the number of different plots includes a plot of curvature vs. time for each FBG sensor selected from the FBG sensors of the optical-fiber stylet.

In some embodiments, the method further includes enabling the FBG sensor-reflected optical signals received from the optical-fiber stylet to be algorithmically converted into a displayable shape for the medical device for display on the display screen.

In some embodiments, the distinctive change in the strain of the optical-fiber stylet is an instantaneous increase in a plotted curvature of the optical-fiber stylet followed by an instantaneous decrease in the plotted curvature.

In some embodiments, a magnitude of the instantaneous decrease in the plotted curvature of the optical-fiber stylet is about twice that of the instantaneous increase in the plotted curvature.

In some embodiments, the selection of the FBG sensors is a last three FBG sensors in the distal-end portion of the optical-fiber stylet.

In some embodiments, the method further includes ceasing to advance the tip of the medical device through the vasculature of the patient after determining the tip of the medical device is located in the SVC. The method also includes confirming the tip of the medical device is in the SVC by way of periodic changes in the strain of the optical-fiber stylet sensed by the selection of the FBG sensors. The periodic changes in the strain result from periodic changes in blood flow within the SVC as a heart of the patient beats.

In some embodiments, advancing the tip of the medical device through the vasculature of the patient includes advancing the tip of the medical device through a right internal jugular vein, a right brachiocephalic vein, and into the SVC.

In some embodiments, the medical device is a CVC.

In some embodiments, advancing the tip of the medical device through the vasculature of the patient includes advancing the tip of the medical device through a right basilic vein, a right axillary vein, a right subclavian vein, a right brachiocephalic vein, and into the SVC.

In some embodiments, the medical device is a peripherally inserted central catheter (PICC).

Also disclosed herein is a method for determining a tip of a medical device is located within an SVC of a patient. The method includes, in some embodiments, advancing the tip of the medical device through a vasculature of the patient toward the SVC. The medical device includes an integrated optical-fiber stylet having a number of FBG sensors along at least a distal-end portion of the optical-fiber stylet for shape sensing with a shape-sensing system including the medical device. The method also includes enabling input optical signals to be sent into the optical-fiber stylet while advancing the tip of the medical device through the vasculature of the patient. The method also includes enabling FBG sensor-reflected optical signals to be received from the optical-fiber stylet while advancing the tip of the medical device through the vasculature of the patient. The method also includes enabling the FBG sensor-reflected optical signals received from the optical-fiber stylet to be algorithmically converted into a plot of curvature vs. time for each FBG sensor of the FBG sensors. The method also includes identifying on a display screen of the shape-sensing system an instantaneous increase in strain of the optical-fiber stylet followed by an instantaneous decrease in the strain as sensed by each FBG sensor of a last three FBG sensors in the distal-end portion of the optical-fiber stylet at a moment the tip of the medical device is advanced into the SVC, thereby determining the tip of the medical device is located within the SVC. The method also includes confirming the tip of the medical device is in the SVC by way of periodic changes in the strain of the optical-fiber stylet as sensed by the last three FBG sensors in the distal-end portion of the optical-fiber stylet. The periodic changes in the strain result from periodic changes in blood flow within the SVC as a heart of the patient beats.

These and other features of the concepts provided herein will become more apparent to those of skill in the art in view of the accompanying drawings and following description, which describe particular embodiments of such concepts in greater detail.

DRAWINGS

Figure 10:
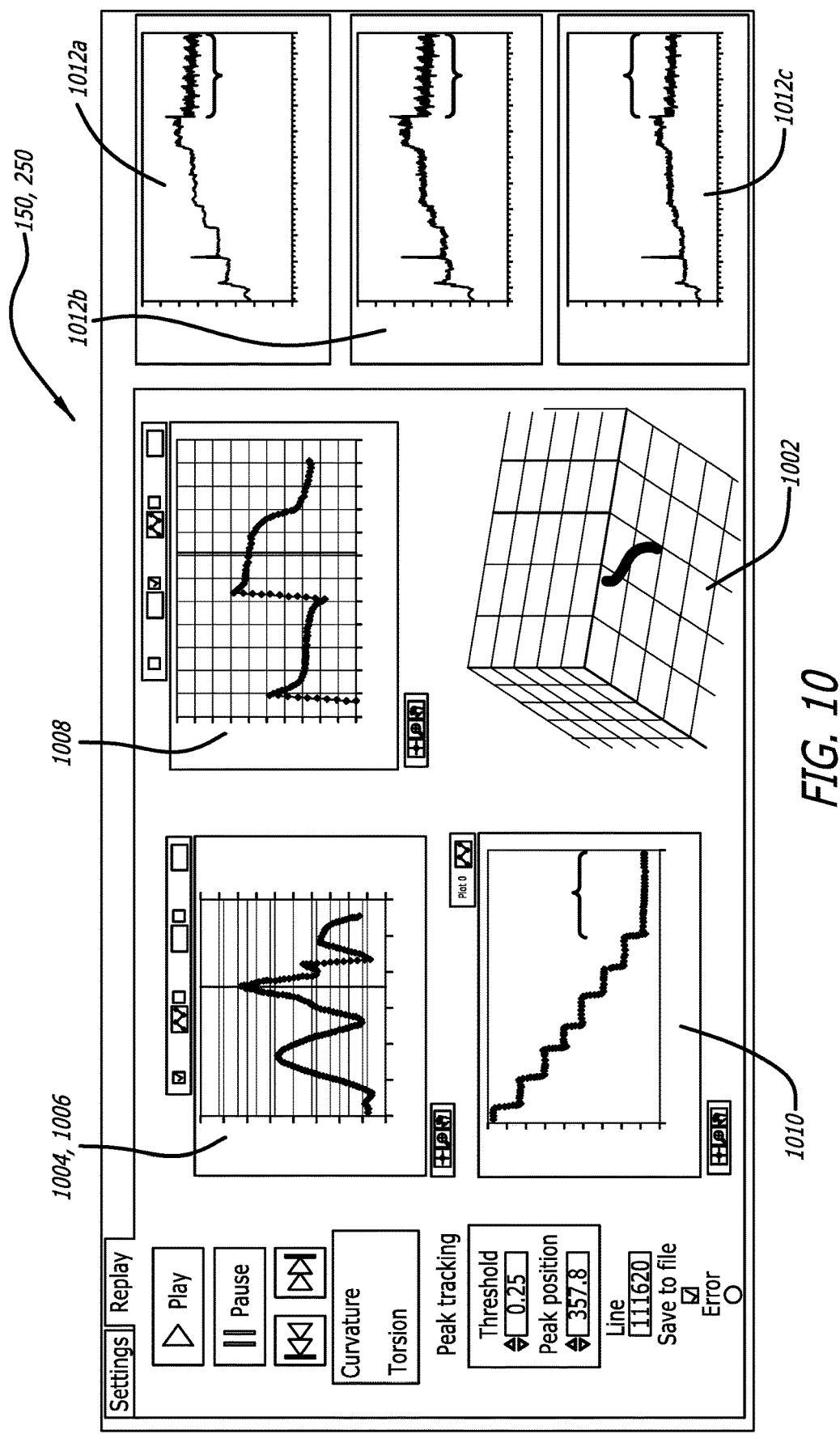

FIG. 10 provides a number of different plots on a display screen of a shape-sensing system in accordance with some embodiments.

Figure 11:
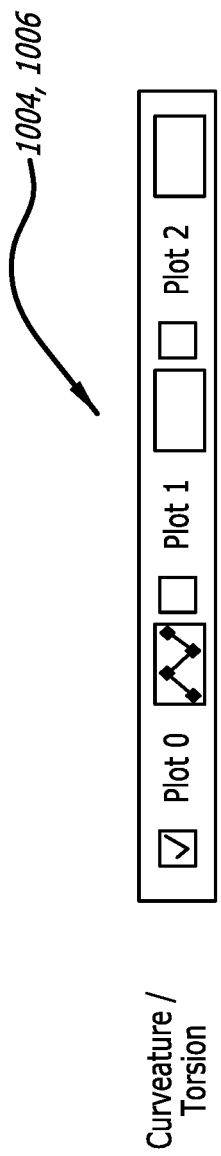

FIG. 11 provides a detailed plot of curvature vs. arc length and torsion vs. arc length for at least a distal-end portion of an optical-fiber stylet as one of the plots of FIG. 10.

Figure 12:
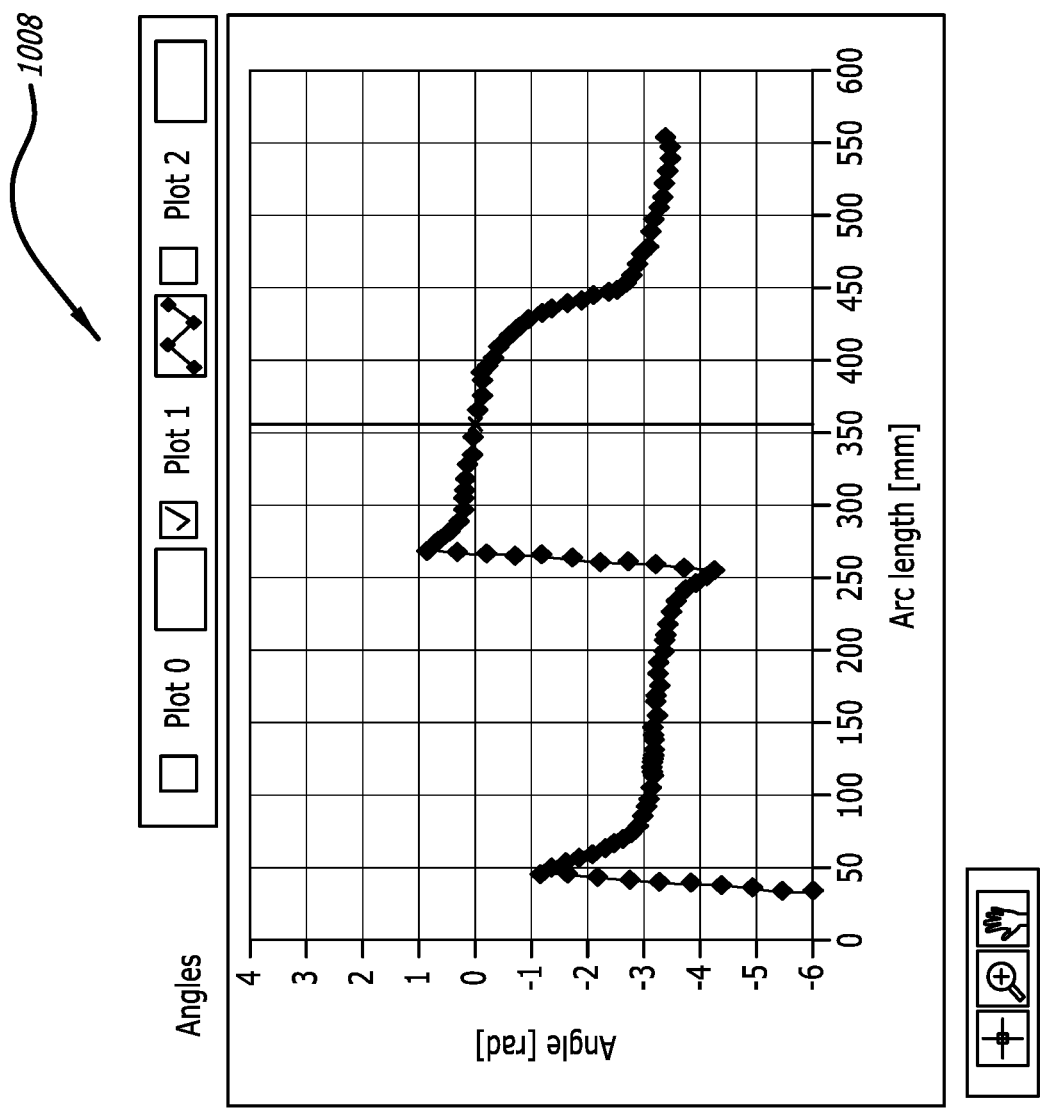

FIG. 12 provides a detailed plot of angle vs. arc length for at least a distal-end portion of an optical-fiber stylet as one of the plots of FIG. 10.

Figure 13:
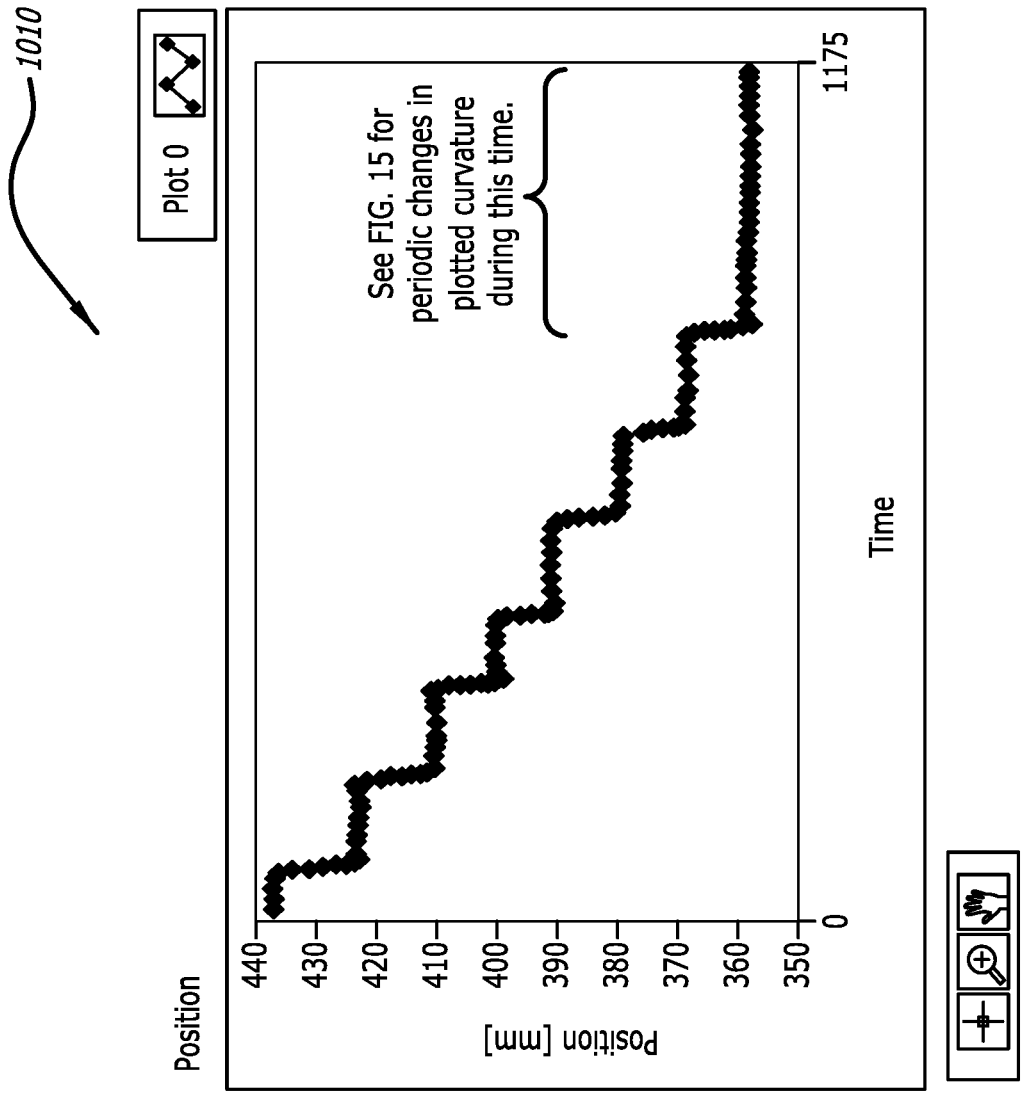

FIG. 13 provides a detailed plot of position vs. time for at least a distal-end portion of an optical-fiber stylet as one of the plots of FIG. 10.

Figure 14:
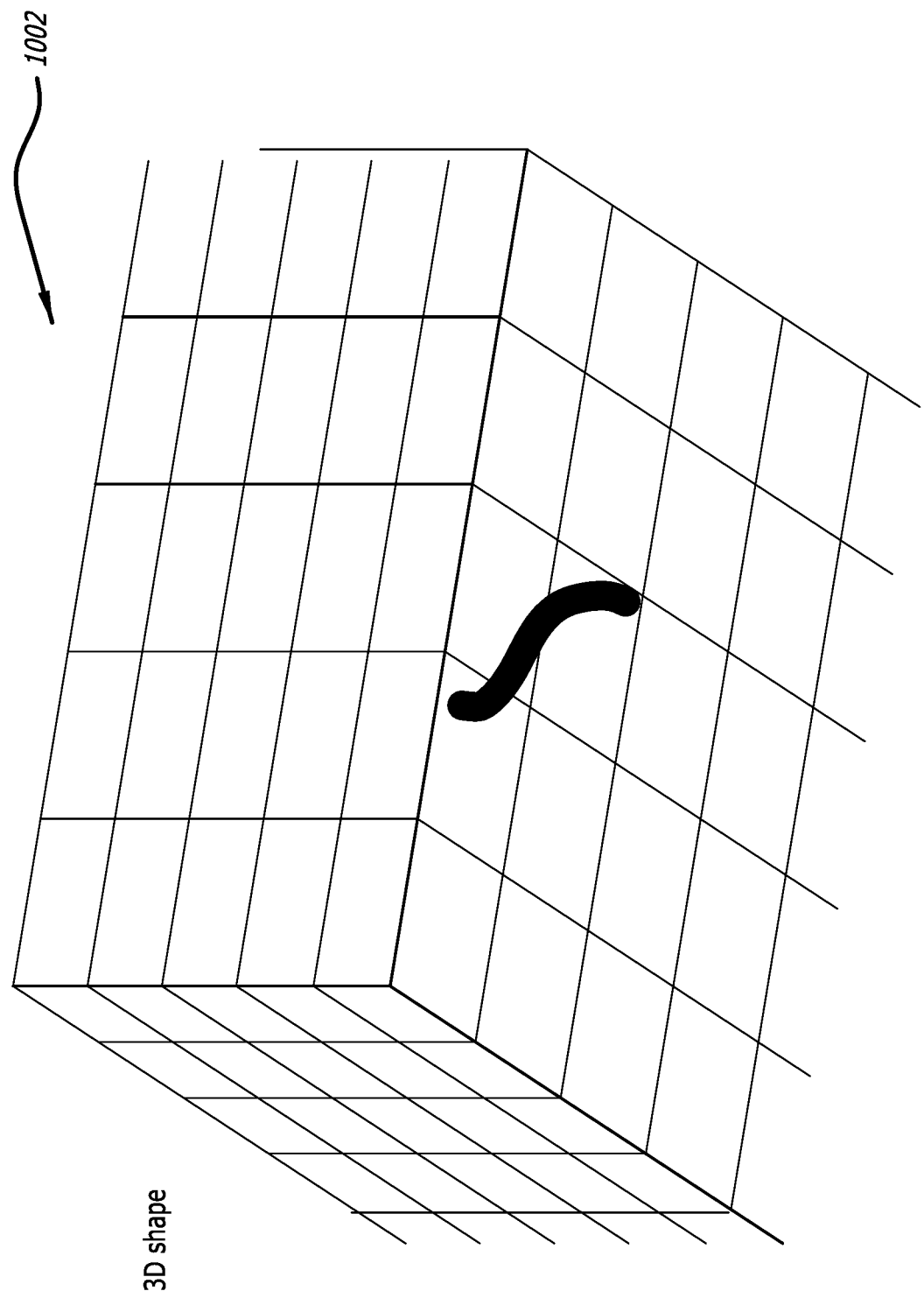

FIG. 14 provides a displayable shape for at least a distal-end portion of a medical device or an optical-fiber stylet in accordance with some embodiments.

Figure 15:
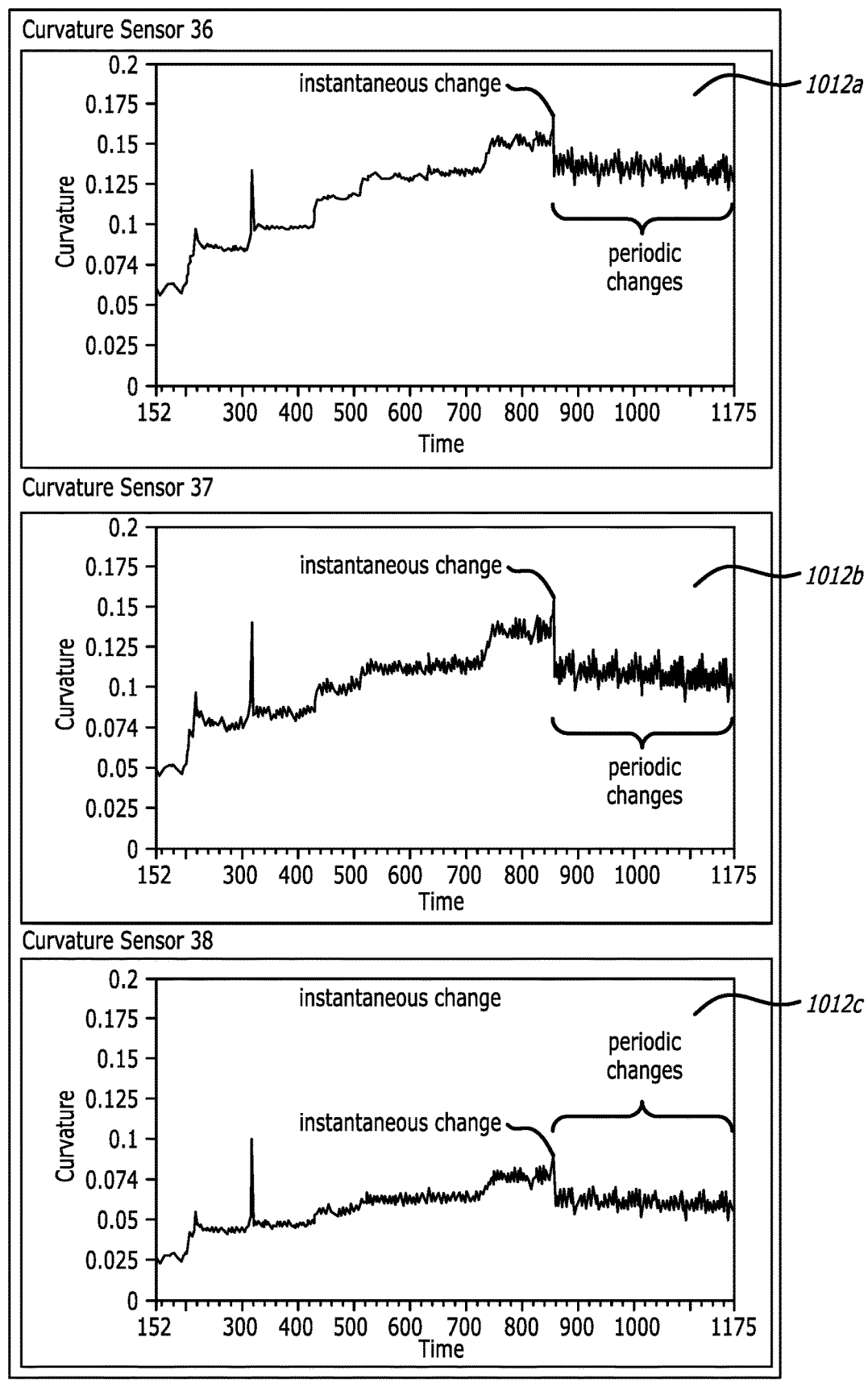

FIG. 15 provides detailed plots of curvature vs. time for each FBG sensor selected from a number of FBG sensors of an optical-fiber stylet as some of the plots of FIG. 10.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

As set forth above, there is a need for clinicians to easily and safely check for displacement of PICCs and CVCs for replacement thereof if necessary. Disclosed herein are shape-sensing system and methods for medical devices that address the foregoing.

For example, a shape-sensing system can include a medical device, an optical interrogator, a console, and a display screen. In one embodiment, the medical device includes an integrated optical-fiber stylet having FBG sensors along at least a distal-end portion of the optical-fiber stylet. As noted above, alternatives to an optical-fiber stylet include, but are not limited or restricted to, an optical-fiber integrated guideway or an optical-fiber integrated guidewire. The optical interrogator is configured to send input optical signals (e.g., broadband incident light) into the optical-fiber stylet and receive FBG sensor-reflected optical signals therefrom.

In some embodiments, the optical-fiber stylet is configured to return information for use in identifying its physical state (e.g., shape length, shape, and/or form) of (i) a portion of the stylet (e.g., tip, segment of stylet, etc.) or a portion of a catheter inclusive of at least a portion of the stylet (e.g., tip, segment of catheter, etc.) or (ii) the entirety or a substantial portion of the stylet or catheter within the body of a patient (hereinafter, described as the "physical state of the stylet" or the "physical state of the catheter"). According to one embodiment of the disclosure, the returned information may be obtained from reflected light signals of different spectral widths, where each reflected light signal corresponds to a portion of broadband incident light propagating along a core of the optical fiber (hereinafter, "core fiber") that is reflected back over the core fiber by a particular sensor located on the core fiber. One illustrative example of the returned information may pertain to a change in signal characteristics of the reflected light signal returned from the sensor, where wavelength shift is correlated to (mechanical) strain on the core fiber. It should be understood that the optical fiber may include or more cores, where an optical fiber including a plurality of cores is referred to as a "multi-core optical fiber."

In some embodiments in which the stylet includes a multi-core optical fiber, each core fiber utilizes a plurality of sensors and each sensor is configured to reflect a different spectral range of the incident light (e.g., different light frequency range). Based on the type and degree of strain asserted on the each core fiber, the sensors associated with that core fiber may alter (shift) the wavelength of the reflected light to convey the type and degree of stain on that core fiber at those locations of the stylet occupied by the sensors. The sensors are spatially distributed at various locations of the core fiber between a proximal end and a distal end of the stylet so that shape sensing of the stylet may be conducted based on analytics of the wavelength shifts. In some embodiments, the shape sensing functionality is paired with the ability to simultaneously pass an electrical signal through the same member (stylet) through conductive medium included as part of the stylet.

More specifically, in some embodiments each core fiber of the multi-core optical fiber is configured with an array of sensors, which are spatially distributed over a prescribed length of the core fiber to generally sense external strain those regions of the core fiber occupied by the sensor. Given that each sensor positioned along the same core fiber is configured to reflect light of a different, specific spectral width, the array of sensors enable distributed measurements throughout the prescribed length of the multi-core optical fiber. These distributed measurements may include wavelength shifts having a correlation with strain experienced by the sensor.

During operation, multiple light reflections (also referred to as "reflected light signals") are returned to the console from each of the plurality of core fibers of the multi-core optical fiber. Each reflected light signal may be uniquely associated with a different spectral width. Information associated with the reflected light signals may be used to determine a three-dimensional representation of the physical state of the stylet within the body of a patient. The core fibers may be spatially separated with the cladding of the optical fiber and each core fiber is configured to separately return light of different spectral widths (e.g., specific light wavelength or a range of light wavelengths) reflected from the distributed array of sensors fabricated in each of the core fibers. A comparison of detected shifts in wavelength of the reflected light returned by a center core fiber (operating as a reference) and the surrounding, periphery core fibers may be used to determine the physical state of the stylet.

During vasculature insertion and advancement of the catheter, the clinician may rely on the console to visualize a current physical state (e.g., shape) of a catheter guided by the stylet to avoid potential path deviations. As the periphery core fibers reside at spatially different locations within the cladding of the multi-mode optical fiber, changes in angular orientation (such as bending with respect to the center core fiber, etc.) of the stylet impose different types (e.g., compression or tension) and degrees of strain on each of the periphery core fibers as well as the center core fiber. The different types and/or degree of strain may cause the sensors of the core fibers to apply different wavelength shifts, which can be measured to extrapolate the physical state of the stylet (catheter).

The console is configured to convert the reflected optical signals into plottable data for displaying plots thereof on the display screen. The plots include a plot of curvature vs. time for each FBG sensor of a selection of the FBG sensors in the distal-end portion of the optical-fiber stylet for identifying a distinctive change in strain of the optical-fiber stylet as a tip of the medical device is advanced into a superior vena cava of a patient.

The console may further be configured to receive one or more electrical signals from the stylet, which as referenced above, may be configured to support both optical connectivity as well as electrical connectivity. The electrical signals may be processed by logic of the console, while being executed by the processor, to determine ECG waveforms for display.

These and other features of the shape-sensing systems and methods provided herein will become more apparent with reference to the accompanying drawings and the following description, which provide particular embodiments of the shape-sensing systems and methods thereof in greater detail.

Shape-Sensing Systems

Figure 1:
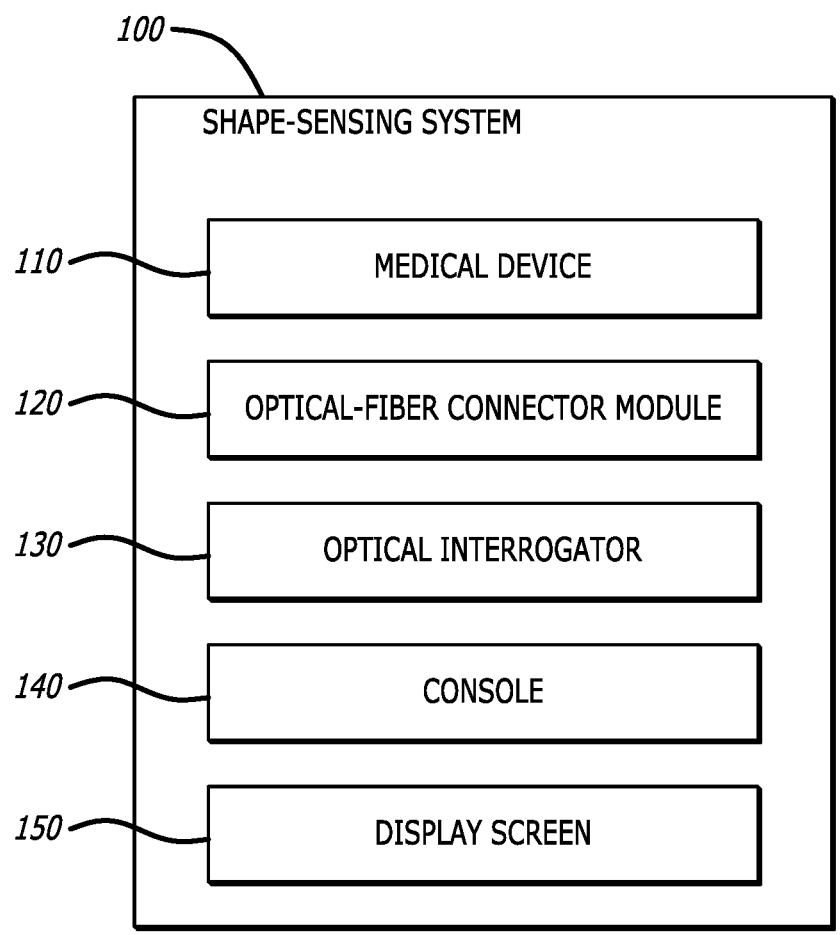
FIG. 1 is a block diagram of a first shape-sensing system in accordance with some embodiments.
Figure 2:
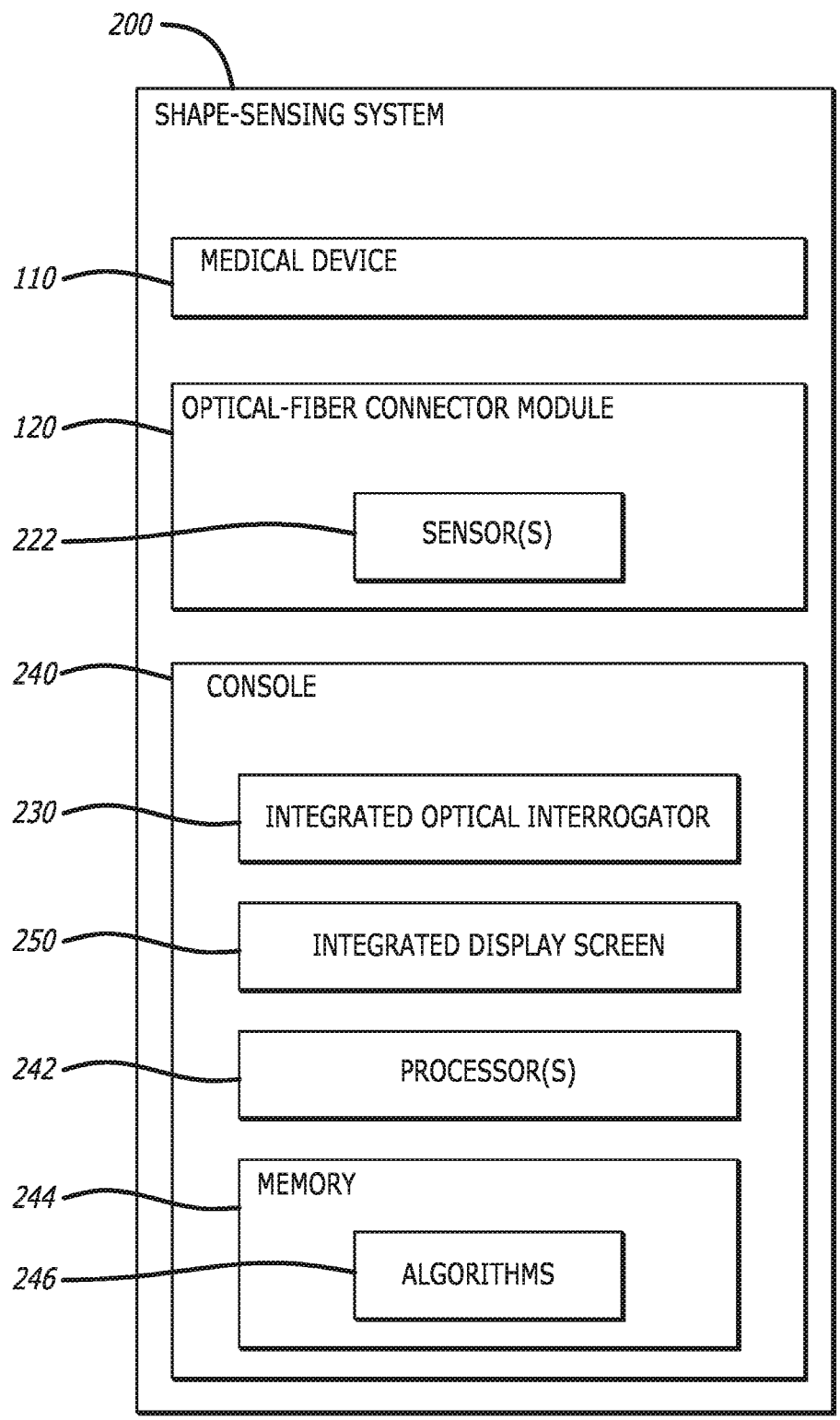
FIG. 2 is a block diagram of a second shape-sensing system in accordance with some embodiments.
Figure 3:
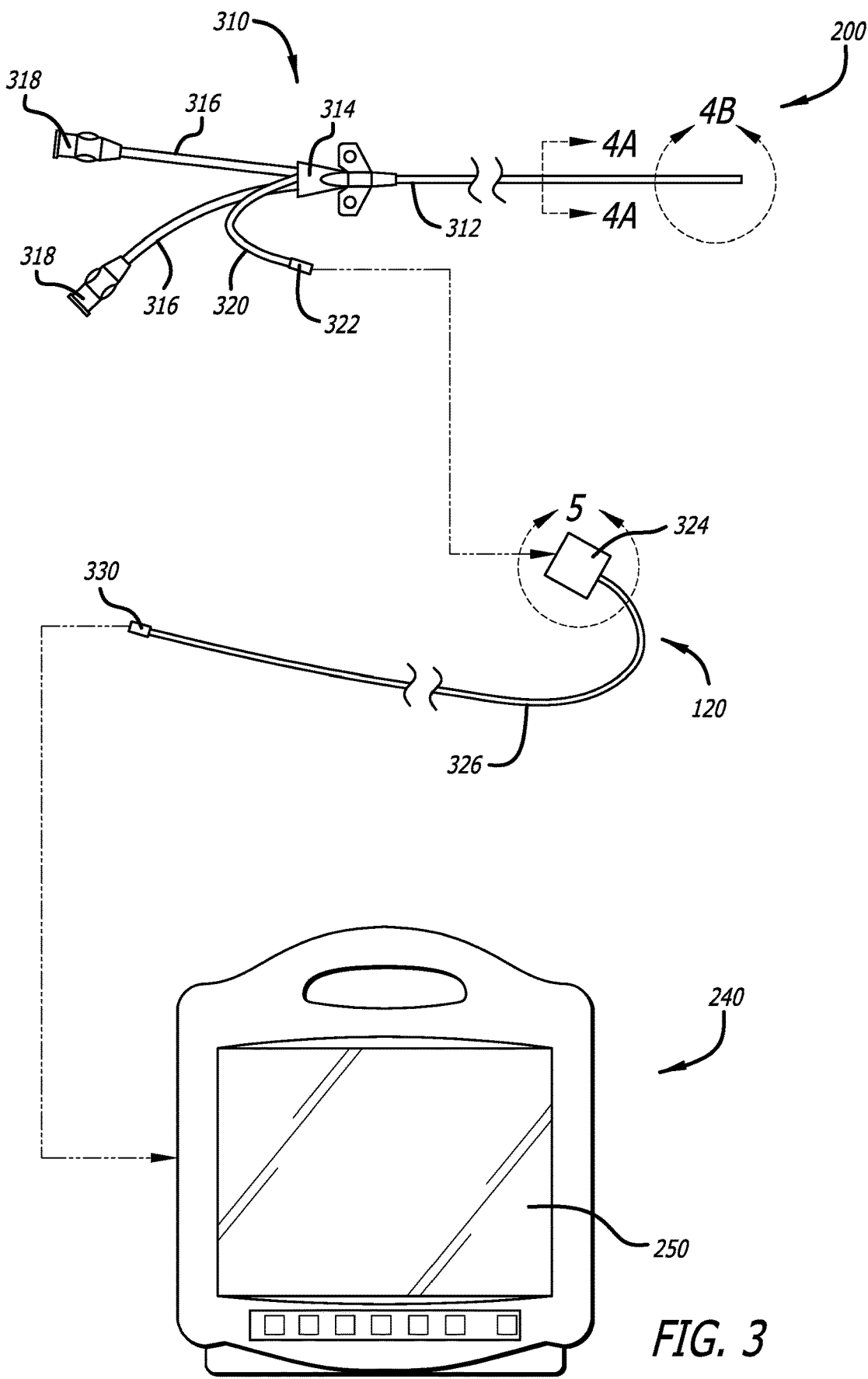
FIG. 3 illustrates the second shape-sensing system in accordance with some embodiments.

FIG. 1 is a block diagram of a first shape-sensing system 100 in accordance with some embodiments. FIG. 2 is a block diagram of a second shape-sensing system 200 in accordance with some embodiments. FIG. 3 illustrates the second shape-sensing system 200 in accordance with some embodiments. FIG. 10 provides a display screen 150 or 250 of the shape-sensing system 100 or 200 in accordance with some embodiments. FIGS. 11-15 provide detailed plots of a number of different plots on the display screen 150 or 250 of FIG. 10.

As shown, the shape-sensing system 100 includes a medical device 110, a stand-alone optical interrogator 130, a console 140, and a display screen 150 such as that of a stand-alone monitor. The shape-sensing system 200 includes the medical device 110, an integrated optical interrogator 230, a console 240, and an integrated display screen 250, wherein both the integrated optical interrogator 230 and the integrated display screen 250 are integrated into the console 240. Each shape-sensing system of the shape-sensing systems 100 and 200 can further include an optical-fiber connector module 120 configured for connecting the medical device 110 to a remainder of the shape-sensing system 100 or 200 such as the optical interrogator 130 or the console 240, which includes the integrated optical interrogator 230.

As set forth in more detail below, the medical device 110 includes an integrated optical-fiber stylet having a number of FBG sensors along at least a distal-end portion of the optical-fiber stylet for shape sensing with the shape-sensing system 100 or 200. (See integrated the optical-fiber stylet 424 in FIG. 4B for an example of the integrated optical-fiber stylet of the medical device 110.)

Certain features of the medical device 110 are set forth in more detail below with respect to particular embodiments of the medical device 110 such as the PICC 310. That said, some features set forth below with respect to one or more embodiments of the medical device 110 are shared among two or more embodiments of the medical device 110. As such, "the medical device 110" is used herein to generically refer to more than one embodiment of the medical device 110 when needed for expository expediency. This is despite certain features having been described with respect to particular embodiments of the medical device 110 such as the PICC 310.

While only shown for the console 240, each console of the consoles 140 and 240 includes one or more processors 242 and memory 244 including a number of algorithms 246 such as one or more optical signal-converter algorithms. The one or more optical signal-converter algorithms are configured to convert FBG sensor-reflected optical signals from the optical-fiber stylet of the medical device 110 into plottable data for displayable shapes corresponding to the medical device 110. The one or more optical signal-convertor algorithms are also configured to convert the reflected optical signals from the optical-fiber stylet of the medical device 110 into plottable data for a number of other plots of the plottable data. The display screen 150 or 250 is configured to display the displayable shapes for the medical device 110 over a 3-dimensional grid 1002 or any plot of the number of plots of the other plottable data.

More specifically, in some embodiments, the algorithms 246 may include shape sensing logic configured to compare wavelength shifts measured by sensors deployed in each outer core fiber at the same measurement region of the stylet, catheter or guidewire (or same spectral width) to the wavelength shift at the center core fiber positioned along central axis and operating as a neutral axis of bending. From these analytics, the shape sensing logic may determine the shape the core fibers have taken in 3D space and may further determine the current physical state of the stylet, catheter or guidewire in 3D space for rendering on the display 150 or 250.

Referring to FIG. 10, the number of plots can include a plot of curvature vs. arc length 1004, a plot of torsion vs. arc length 1006, a plot of angle vs. arc length 1008, or a plot of position vs. time 1010 for at least the distal-end portion of the optical-fiber stylet. The number of plots can further include at least a plot of curvature vs. time 1012a, 1012b, 1012c, . . . , 1012n, for each FBG sensor of a selection of the FBG sensors in the distal-end portion of the optical-fiber stylet. Any one or more of the plots of curvature vs. time 1012a, 1012b, 1012c, . . . , 1012n, for the selection of the FBG sensors in the distal-end portion of the optical-fiber stylet can be used to manually identify a distinctive change in strain of the optical-fiber stylet by way of a distinctive change in plotted curvature of the optical-fiber stylet at a moment a tip of the medical device 110 is advanced into an SVC of a patient. However, the three plots of curvature vs. time 1012a, 1012b, and 1012c shown in FIGS. 10 and 15 are those for a last three FBG sensors in the distal-end portion of the optical-fiber stylet. The last three FBG sensors in the distal-end portion of the optical-fiber stylet are particularly useful in identifying the distinctive change in the plotted curvature of the optical-fiber stylet in that the foregoing FBG sensors directly experience a physical change in curvature resulting from tensile strain and compressive strain of the optical-fiber stylet when the tip of the medical device 110 is advanced into the SVC of the patient. The distinctive change in the plotted curvature of the optical-fiber stylet is exemplified by an instantaneous increase in the plotted curvature followed by an instantaneous decrease in the plotted curvature having a magnitude about twice that of the instantaneous increase in the plotted curvature as shown by the arrow in any plot 1012a, 1012b, or 1012c of curvature vs. time shown in FIG. 15.

In addition to being able to use any one or more of the plots of curvature vs. time to manually identify the distinctive change in the strain of the optical-fiber stylet at the moment the tip of the medical device 110 is advanced into the SVC of the patient, any one or more of the plots of curvature vs. time 1012a, 1012b, 1012c, . . . , 1012n, for the selection of the FBG sensors in the distal-end portion of the optical-fiber stylet can be used to manually confirm the tip of the medical device 110 is in the SVC by way of periodic changes in the strain of the optical-fiber stylet. The periodic changes in the strain of the optical-fiber stylet are evidenced by periodic changes in the plotted curvature of the optical-fiber stylet sensed by the selection of the FBG sensors. (See the three plots of curvature vs. time 1012a, 1012b, and 1012c in FIGS. 10 and 15, between about 860 s and 1175 s when the distal-end portion of the optical-fiber stylet is held in position in the SVC as shown by the plot of position vs. time 1010.) The periodic changes in the plotted curvature result from periodic changes in blood flow within the SVC sensed by the selection of the FBG sensors as a heart of the patient beats.

Each console of the consoles 140 and 240 can further include an SVC-determiner algorithm of the one or more algorithms 246 configured to automatically determine the distinctive change in the strain of the optical-fiber stylet by way of a distinctive change in plotted curvature of the optical-fiber stylet, or the plottable data therefor, at the moment the tip of the medical device 110 is advanced into the SVC of the patient. Again, the distinctive change in the plotted curvature is an instantaneous increase in the plotted curvature followed by an instantaneous decrease in the plotted curvature having a magnitude about twice that of the instantaneous increase in the plotted curvature. The SVC-determiner algorithm can also be configured to confirm the tip of the medical device 110 is in the SVC by way of automatically determining periodic changes in the plotted curvature of the optical-fiber stylet sensed by the selection of the FBG sensors. (See the three plots of curvature vs. time 1012a, 1012b, and 1012c in FIGS. 10 and 15, between about 860 s and 1175 s when the distal-end portion of the optical-fiber stylet is held in position in the SVC as shown by the plot of position vs. time 1010.) The periodic changes in the plotted curvature result from periodic changes in blood flow within the SVC sensed by the selection of the FBG sensors as a heart of the patient beats.

The optical interrogator 130 or 230 is configured to send input optical signals into the optical-fiber stylet of the medical device 110 and receive the reflected optical signals from the optical-fiber stylet. When the optical-fiber connector module 120 is present in the shape-sensing system 100 or 200, the optical interrogator 130 or 230 is configured to send the input optical signals into the optical-fiber stylet of the medical device 110 by way of the optical-fiber connector module 120 and receive the reflected optical signals from the optical-fiber stylet by way of the optical-fiber connector module 120.

In some embodiments, the optical interrogator 130 or 230 may be a photodetector such as a positive-intrinsic-negative "PIN" photodiode, avalanche photodiode, etc. With respect to such embodiments, the optical interrogator 130 or 230 may be configured to: (i) receive returned optical signals, namely reflected light signals received from optical fiber-based reflective gratings (sensors) fabricated within each of the core fibers deployed within a stylet, catheter, guidewire, etc., and (ii) translate the reflected light signals into reflection data, namely data in the form of electrical signals representative of the reflected light signals including wavelength shifts caused by strain. The reflected light signals associated with different spectral widths include reflected light signals provided from sensors positioned in the center core fiber (reference) of a multi-core optical fiber of the stylet, catheter, guidewire, etc., and reflected light signals provided from sensors positioned in the outer core fibers of the stylet, catheter, guidewire, etc.

The optical-fiber connector module 120 includes a housing 324, a cable 326 extending from the housing 324, and an optical fiber 528 within at least the cable 326. (For the optical fiber 528, see FIG. 5.) The optical-fiber connector module 120 is configured to establish a first optical connection between the optical-fiber stylet of the medical device 110 and the optical fiber 528 of the optical-fiber connector module 120. The optical-fiber connector module 120 is also configured with a plug 330 at a terminus of the cable 326 to establish a second optical connection between the optical fiber 528 of the optical-fiber connector module 120 and the optical interrogator 130 or 230. The optical fiber 528 of the optical-fiber connector module 120 is configured to convey the input optical signals from the optical interrogator 130 or 230 to the optical-fiber stylet of the medical device 110 and the reflected optical signals from the optical-fiber stylet to the optical interrogator 130 or 230.

The optical-fiber connector module 120 can further include one or more sensors 222 selected from at least a gyroscope, an accelerometer, and a magnetometer disposed within the housing 324. The one or more sensors 222 are configured to provide sensor data to the console 140 or 240 by way of one or more data wires within at least the cable 326 for determining a reference plane with a reference plane-determiner algorithm of the one or more algorithms 246 for shape sensing with the optical-fiber stylet of the medical device 110.

Certain features of the optical-fiber connector module 120 are set forth in more detail below with respect to particular embodiments of the optical-fiber connector module 120 such as the optical-fiber connector module 620 and 820. That said, some features set forth below with respect to one or more embodiments of the optical-fiber connector module 120 are shared among two or more embodiments of the optical-fiber connector module 120. As such, "the optical-fiber connector module 120" is used herein to generically refer to more than one embodiment of the optical-fiber connector module 120 when needed for expository expediency. This is despite certain features having been described with respect to particular embodiments of the optical-fiber connector module 120 such as the optical-fiber connector modules 620 and 820.

Medical Devices

Figure 4A:
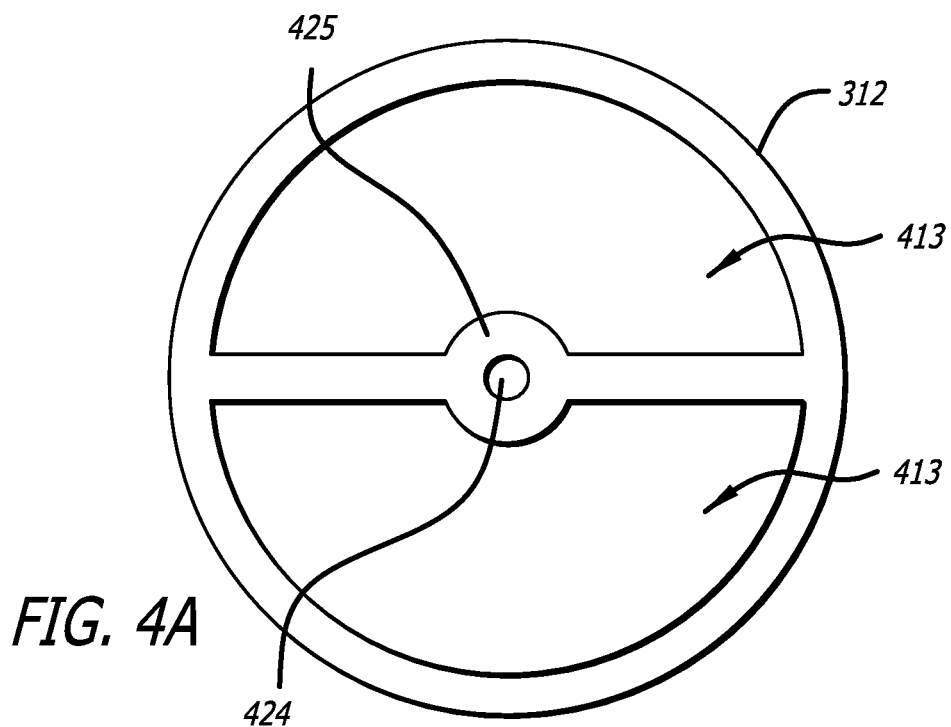
FIG. 4A illustrates a transverse cross-section of a catheter tube of a medical device in accordance with some embodiments.
Figure 4B:
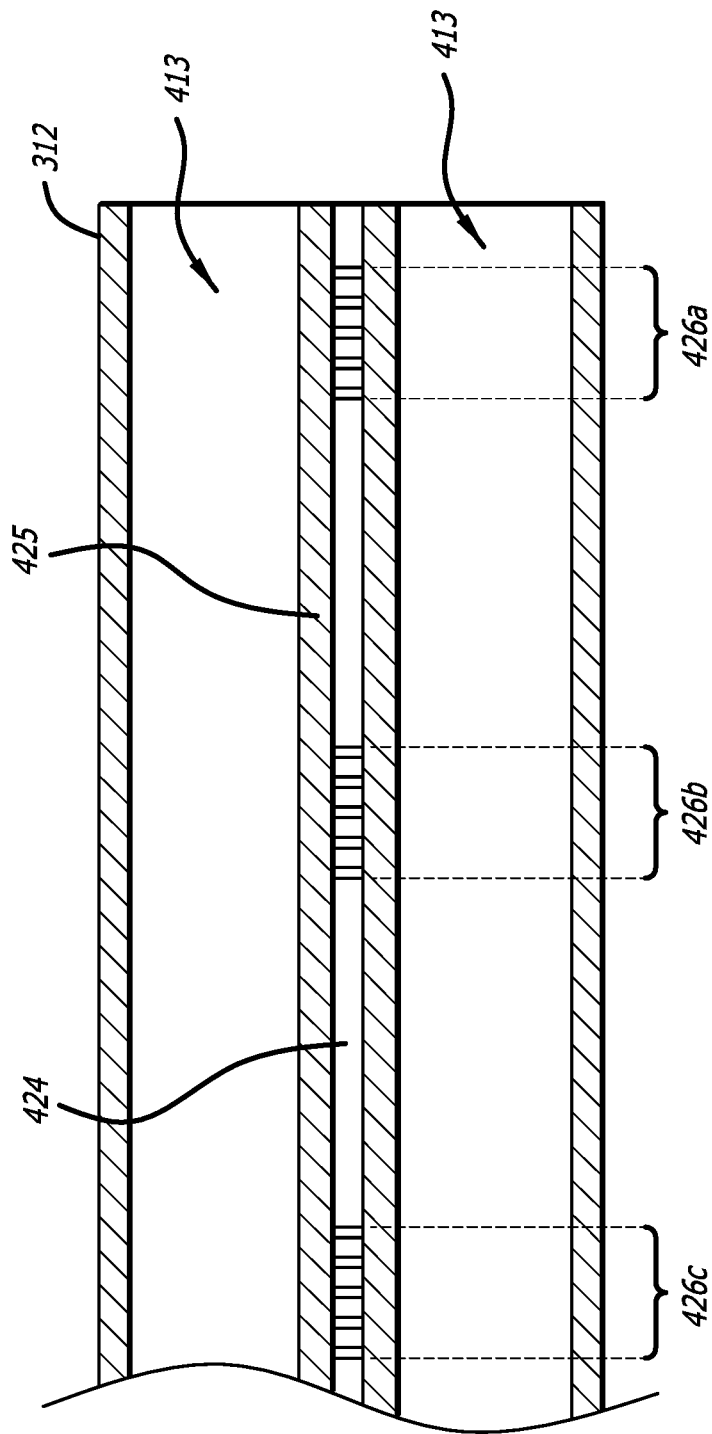
FIG. 4B illustrates a longitudinal cross-section of the catheter tube of the medical device in accordance with some embodiments.

FIG. 3 also illustrates a PICC 310 as the medical device 110 in accordance with some embodiments. FIG. 4A illustrates a transverse cross-section of a catheter tube 312 of the PICC 310 including an integrated optical-fiber stylet 424 in accordance with some embodiments. FIG. 4B illustrates a longitudinal cross-section of the catheter tube 312 of the PICC 310 including the integrated optical-fiber stylet 424 in accordance with some embodiments.

As shown, the PICC 310 includes the catheter tube 312, a bifurcated hub 314, two extension legs 316, and two Luer connectors 318 operably connected in the foregoing order. The catheter tube 312 includes two catheter-tube lumens 413 and the optical-fiber stylet 424 disposed in a longitudinal bead 425 of the catheter tube 312 such as between the two catheter-tube lumens 413, as extruded. In some embodiments, the optical-fiber stylet 424 includes a single core fiber. In other embodiments, the optical-fiber stylet 424 is a multi-core optical fiber stylet. Optionally, in a same or different longitudinal bead of the catheter tube 312, the PICC 310 can further include an electrocardiogram ("ECG") stylet. The bifurcated hub 314 has two hub lumens correspondingly fluidly connected to the two catheter-tube lumens 413. Each extension leg of the two extension legs 316 has an extension-leg lumen fluidly connected to a hub lumen of the two hub lumens. The PICC 310 further includes a stylet extension tube 320 extending from the bifurcated hub 314. The stylet extension tube 320 can be a skived portion of the catheter tube 312 including the optical-fiber stylet 424 or the skived portion of the catheter tube 312 disposed in another tube, either of which can terminate in a plug 322 for establishing an optical connection between the optical fiber 528 of the optical-fiber connector module 120 and the optical-fiber stylet 424 of the PICC 310.

The optical-fiber stylet 424 includes a number of FBG sensors 426a, 426b, 426c, . . . , 426n along at least a distal-end portion of the optical-fiber stylet 424 configured for shape sensing with the shape-sensing system 100 or 200. The FBG sensors 426a, 426b, 426c, . . . , 426n include periodic variations in refractive index of the optical fiber of the optical-fiber stylet 424, thereby forming wavelength-specific reflectors configured to reflect the input optical signals sent into the optical-fiber stylet 424 by the optical interrogator 130 or 230. In embodiments in which the optical-fiber stylet 424 is a multi-core optical fiber stylet, each core fiber includes a number of FBG sensors 426a, 426b, 426c, . . . , 426n, FIG. 4B illustrates, in particular, a last three FBG sensors 426a, 426b, and 426c in the distal-end portion of the optical-fiber stylet 424, which FBG sensors 426a, 426b, and 426c, which in some embodiments, are particularly useful in identifying a distinctive change in plotted curvature of the optical-fiber stylet 424 as set forth above. This is because the last three FBG sensors 426a, 426b, and 426c directly experience a physical change in curvature of the optical-fiber stylet 424 when, in this case, a tip of the PICC 310 is advanced into an SVC of a patient. However, in other embodiments, reflected light received from FBG sensors in addition, or as an alternative, to the distal-most three FBG sensors 426a, 426b, and 426c may be used in shape sensing functionalities of the shape-sensing system 100 or 200.

While the PICC 310 is provided as a particular embodiment of the medical device 110 of the shape-sensing system 100 or 200, it should be understood that any medical device of a number of medical devices including catheters such as a CVC can include at least an optical-fiber stylet and a stylet extension tube terminating in a plug for establishing an optical connection between the optical-fiber stylet of the medical device and the optical interrogator 130 or 230, optionally by way of the optical fiber 528 of the optical-fiber connector module 120.

Optical-Fiber Connector Modules

Figure 5:
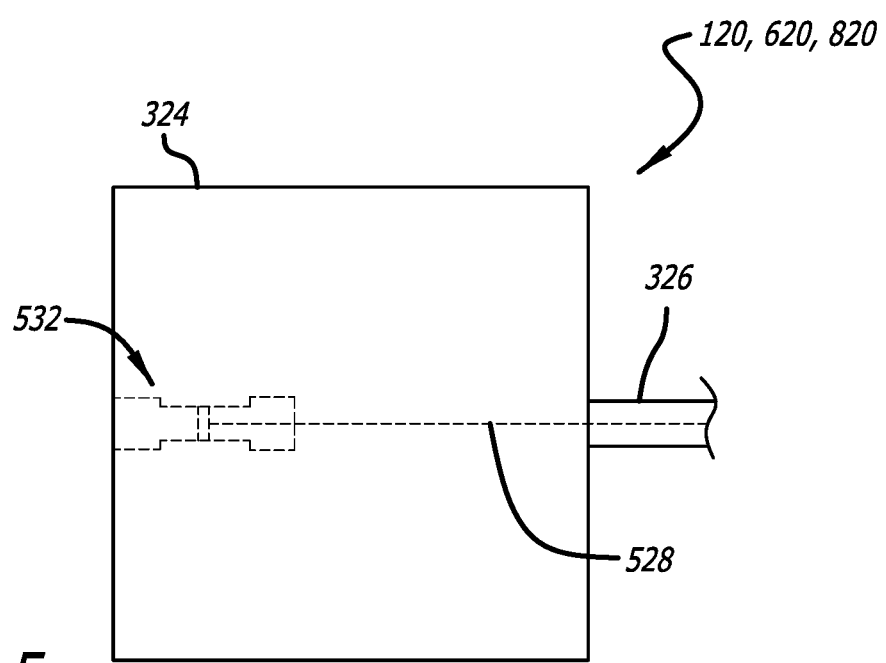
FIG. 5 illustrates a detailed section of an optical-fiber connector module in accordance with some embodiments.
Figure 6:
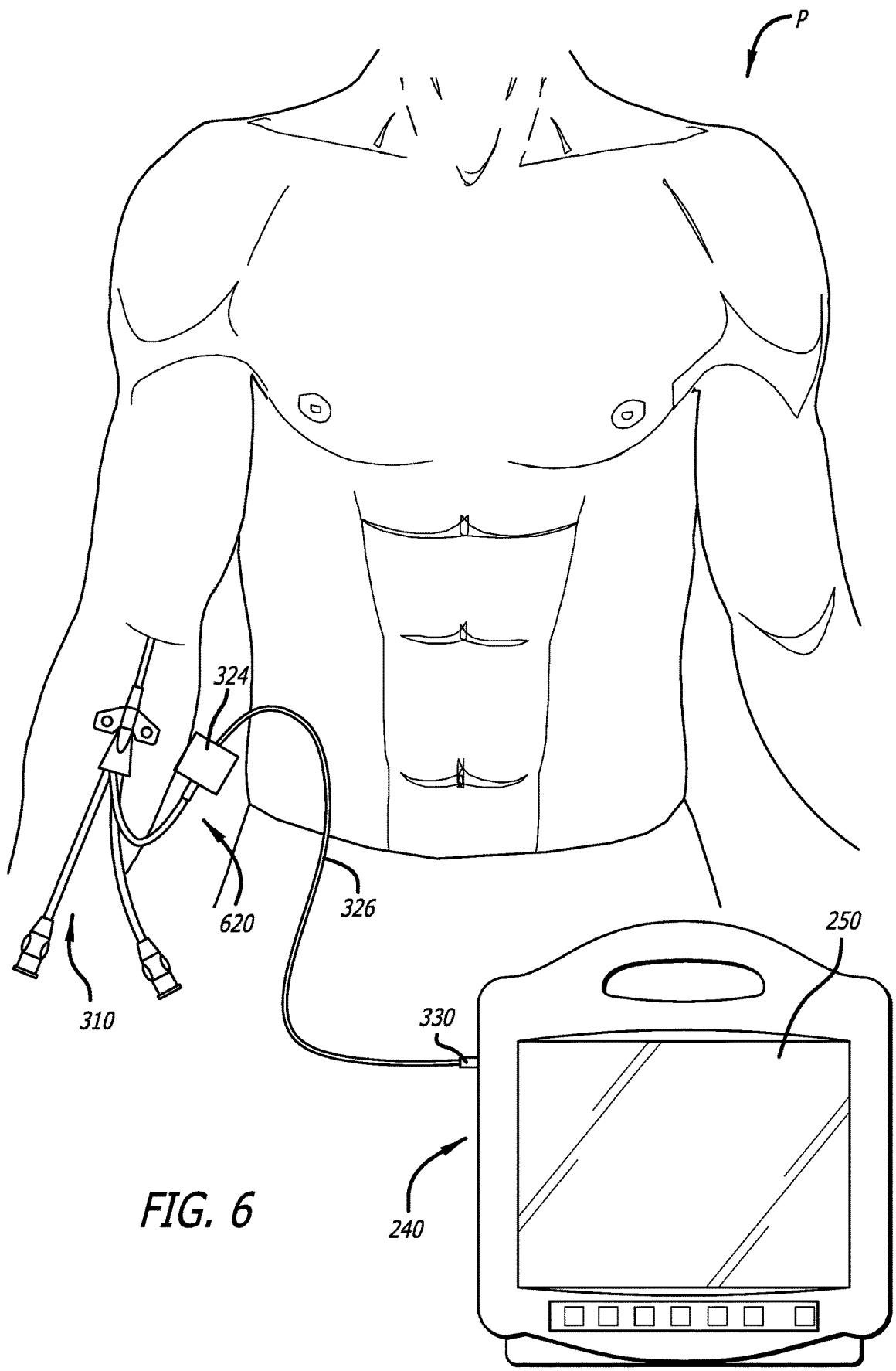
FIG. 6 illustrates the second shape-sensing system with a first optical-fiber connector module in accordance with some embodiments.
Figure 7:
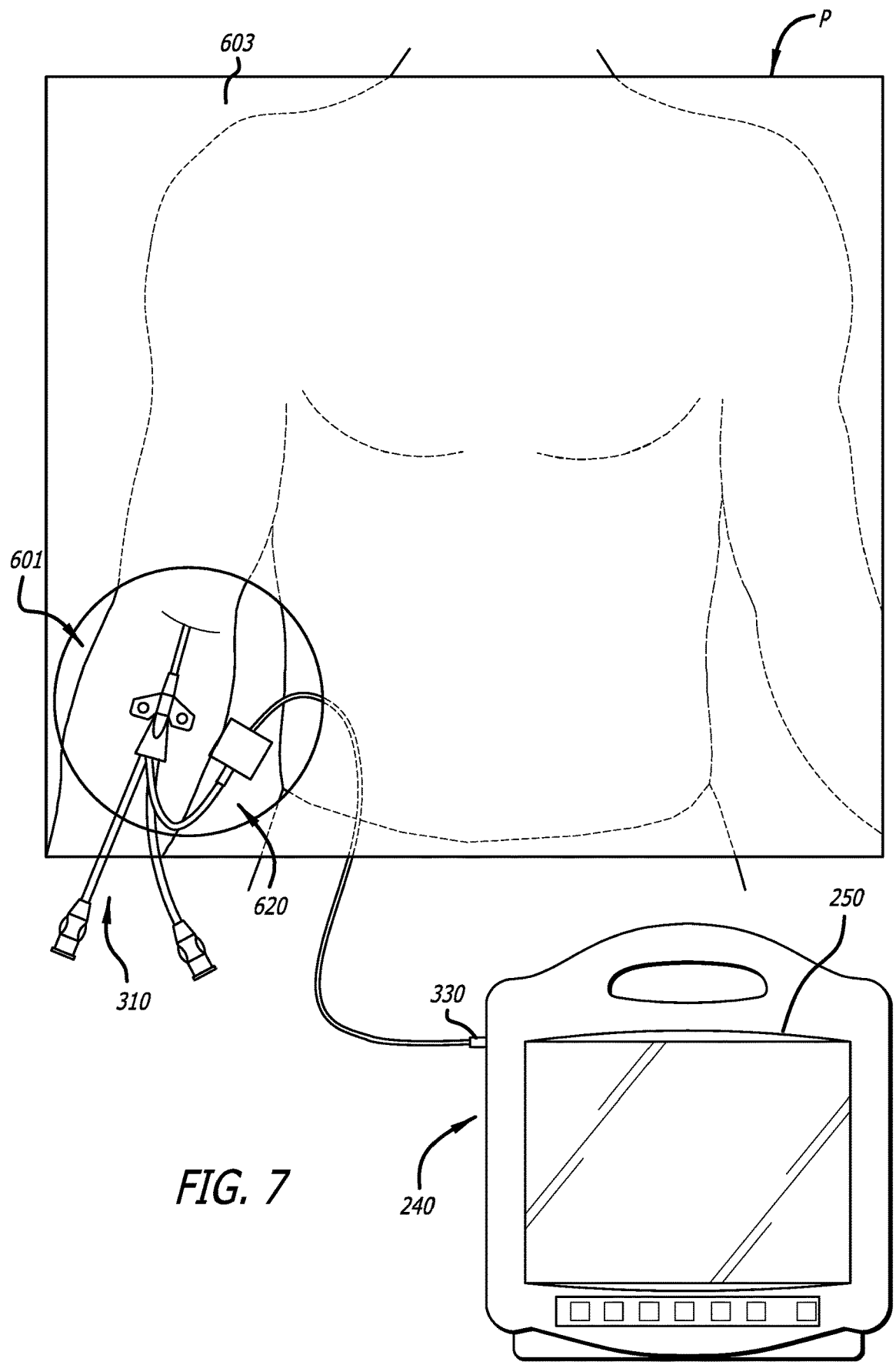
FIG. 7 illustrates the second shape-sensing system with the first optical-fiber connector module within a fenestration of a surgical drape in accordance with some embodiments.
Figure 8:
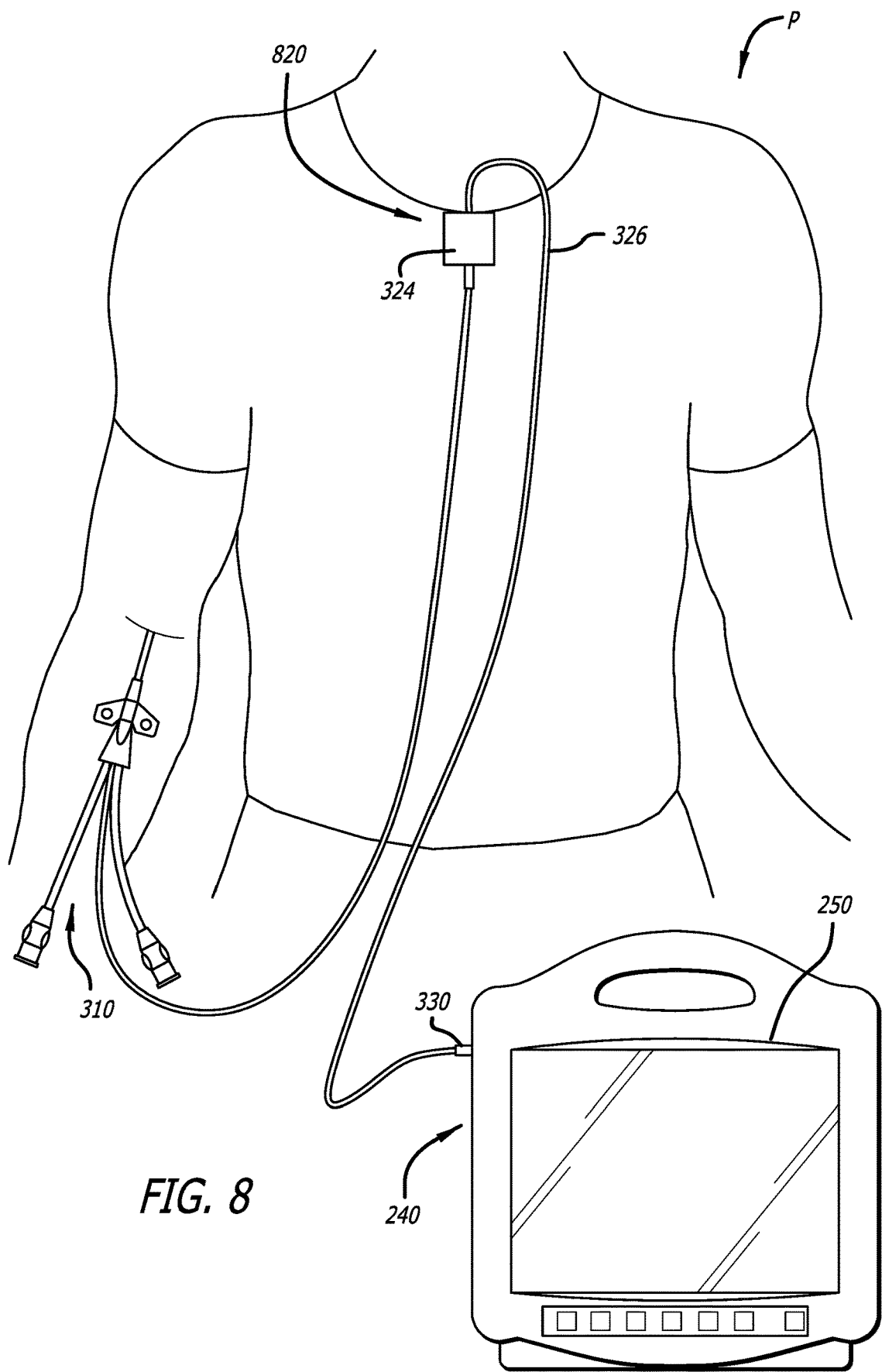
FIG. 8 illustrates the second shape-sensing system with a second optical-fiber connector module in accordance with some embodiments.
Figure 9:
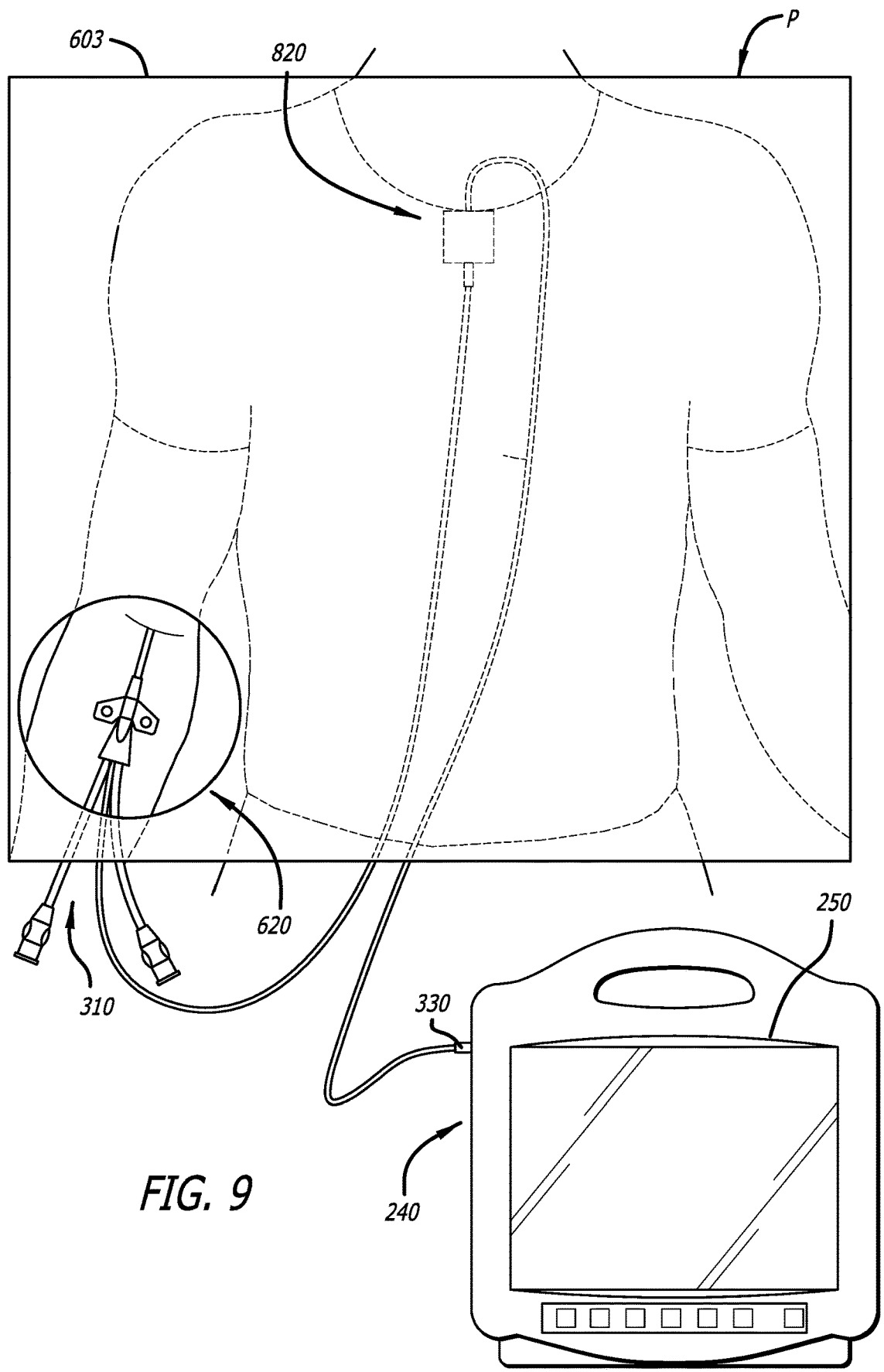
FIG. 9 illustrates the second shape-sensing system with the second optical-fiber connector module beneath a surgical drape in accordance with some embodiments.

FIG. 6 illustrates the second shape-sensing system 200 with a first optical-fiber connector module 620 in accordance with some embodiments. FIG. 7 illustrates the second shape-sensing system 200 with the first optical-fiber connector module 620 within a fenestration 601 of a surgical drape 603 in accordance with some embodiments. FIG. 8 illustrates the second shape-sensing system 200 with a second optical-fiber connector module 820 in accordance with some embodiments. FIG. 9 illustrates the second shape-sensing system 200 with the second optical-fiber connector module 820 beneath the surgical drape 603 in accordance with some embodiments. FIG. 5 illustrates a detailed section of the optical-fiber connector module 120 in accordance with some embodiments thereof such as the first optical-fiber connector module 620 or the second optical-fiber connector module 820.

As shown, the optical-fiber connector module 620 or 820 includes the housing 324, a receptacle 532 disposed in the housing 324, the cable 326 extending from the housing 324, and an optical fiber 528 within at least the cable 326.

The receptacle 532 includes an optical receiver configured to accept insertion of an optical terminal of a plug of the medical device 110 (e.g., the plug 322 of the PICC 310) for establishing an optical connection between the optical-fiber connector module 620 or 820 and the optical-fiber stylet of the medical device 110 (e.g., the optical-fiber stylet 424 of the PICC 310) when the plug is inserted into the receptacle 532.

The cable 326 includes the plug 330 for establishing an optical connection between the optical-fiber connector module 620 or 820 and the optical interrogator 230 of the console 240.

The optical fiber 528 extends from the receptacle 532 through the cable 326 to the plug 330. The optical fiber 528 is configured to convey the input optical signals from the optical interrogator 230 to the optical-fiber stylet of the medical device 110 (e.g., the optical-fiber stylet 424 of the PICC 310) and the reflected optical signals from the optical-fiber stylet to the optical interrogator 230.

As set forth above, the optical-fiber connector module 620 or 820 can further include the one or more sensors 222 selected from the gyroscope, the accelerometer, and the magnetometer disposed within the housing 324. The one or more sensors 222 are configured to provide sensor data for determining a reference plane for shape sensing with the optical-fiber stylet of the medical device 110 (e.g., the optical-fiber stylet 424 of the PICC 310).

While not shown, the optical-fiber connector module 620 or 820 can further include power and data wires extending from the one or more sensors 222 through the cable 326 to the plug 330 or another plug. The power and data wires are configured to respectively convey power to the one or more sensors 122 and data from the one or more sensors 122 to the console 240 when the one or more sensors 122 are present in the optical-fiber connector module 620 or 820.

The optical-fiber connection module 620 is configured to sit within the fenestration 601 of the surgical drape 603 adjacent a percutaneous insertion site for the medical device 110 (e.g., a catheter such as the PICC 310). As the optical-fiber connection module 620 is configured to sit within the fenestration 601 of the surgical drape 603, the optical-fiber connection module 620 is amenable to disinfection or sterilization. For example, the housing 324 of the optical-fiber connection module 620 can be a non-porous or chemically resistant to oxidants. The optical-fiber connection module 620 can be configured for manual disinfection with a ChloraPrep® product by Becton, Dickinson and Company (Franklin Lakes, NJ), or the optical-fiber connection module 620 can be configured for automatic high-level disinfection or sterilization with vaporized $H_2O_2$ by way of Trophon® by Nanosonics Inc. (Indianapolis, IN).

In contrast to the optical-fiber connection module 620, the optical-fiber connection module 820 is configured to sit beneath the surgical drape 603 on a chest of a patient P. As such, the optical-fiber connection module 820 need not require a same level of disinfection or sterilization as the optical-fiber connection module 620.

While not shown, the housing 324 the optical-fiber connection module 820 includes a loop extending from the housing 324, a tether point integrated into the housing 324, a ball-lock-pin receiver integrated into the housing 324, or the like configured for attaching a neck strap to the optical-fiber connector module 820. The loop, the tether point, the ball-lock-pin receiver, or the like enables the optical-fiber connector module 820 to be secured to a neck of the patient P while sitting on the patient's chest. Additionally or alternatively, the housing 324 includes a patient-facing surface (e.g., a back of the optical-fiber connection module 820) configured to be adhered to the patient's chest. The patient-facing surface enables the optical-fiber connector module 820 to be secured to the patient's chest while sitting on the patient's chest whether or not the optical-fiber connection module 820 is also secured to the patient's neck.

Again, the receptacle 532 includes an optical receiver configured to accept insertion of an optical terminal of a plug of the medical device 110 (e.g., the plug 322 of the PICC 310) and form an optical connection when the plug is inserted into the receptacle 532; however, with the optical-fiber connector module 820, the optical connection is formed with the surgical drape 603 between the optical-fiber connector module 820 and the medical device 110. The receptacle 532 and the plug of the medical device 110 enable at least the optical connection from a sterile field (e.g., above the surgical drape 603) including the medical device 110 such as the PICC 310 to a non-sterile field (e.g., beneath the surgical drape 603) including the optical-fiber connection module 820 by way of breaching the surgical drape 603.

Methods

Each method of a number of methods for determining whether the tip of the medical device 110 is located within an SVC of a patient includes advancing the tip of the medical device 110 through a vasculature of the patient toward the SVC. As set forth above, the medical device 110 (e.g., the PICC 310) includes the integrated optical-fiber stylet (e.g., the optical-fiber stylet 424) having the number of FBG sensors (e.g. the FBG sensors 426a, 426b, 426c, . . . , 426n) along at least the distal-end portion of the optical-fiber stylet for shape sensing with the shape-sensing system 100 or 200 including the medical device 110. When the medical device 110 is the PICC 310, advancing the tip of the PICC 310 through the vasculature of the patient includes advancing the tip of the PICC 310 through a right internal jugular vein, a right brachiocephalic vein, and into the SVC. When the medical device is a CVC, advancing the tip of the CVC through the vasculature of the patient includes advancing the tip of the DVC through a right basilic vein, a right axillary vein, a right subclavian vein, a right brachiocephalic vein, and into the SVC.

The method can include enabling certain functions of the shape-sensing system 100 or 200 by turning on the console 140 or 240, running one or more programs on the console 140 or 240, making the selection of the FBG sensors (e.g., a selection of the FBG sensors 426a, 426b, 426c . . . , 426n) in the distal-end portion of the optical-fiber stylet for the plots of curvature vs. time 1012a, 1012b, 1012c, . . . , 1012n, making the optical or electrical connections, or the like as needed for various functions of the shape-sensing system 100 or 200. Enabling certain functions of the shape-sensing system 100 or 200 can include enabling the input optical signals to be sent into the optical-fiber stylet by the optical interrogator 130 or 230 of the shape-sensing system 100 or 200 while advancing the tip of the medical device 110 through the vasculature of the patient. Enabling certain functions of the shape-sensing system 100 or 200 can include enabling the FBG sensor-reflected optical signals to be received from the optical-fiber stylet by the optical interrogator 130 or 230 while advancing the tip of the medical device 110 through the vasculature of the patient. Enabling certain functions of the shape-sensing system 100 or 200 can include enabling the FBG sensor-reflected optical signals received from the optical-fiber stylet to be algorithmically converted into the number of different plots (e.g., the plot of curvature vs. arc length 1004, the plot of torsion vs. arc length 1006, the plot of angle vs. arc length 1008, the plot of position vs. time 1010, one or more of the plots of curvature vs. time 1012a, 1012b, 1012c . . . , 1012n, etc.) for display on the display screen 150 or 250. Enabling certain functions of the shape-sensing system 100 or 200 can include enabling the FBG sensor-reflected optical signals received from the optical-fiber stylet to be algorithmically converted into the displayable shapes over the 3-dimensional grid 1002 for the medical device 110 for display on the display screen 150 or 250.

The method can include manually identifying on the display screen 150 or 250 the distinctive change in the plotted curvature of the optical-fiber stylet sensed by the selection of the FBG sensors in the distal-end portion of the optical-fiber stylet at the moment the tip of the medical device 110 is advanced into the SVC, thereby determining the tip of the medical device 110 is located within the SVC. Identifying on the display screen 150 or 250 the distinctive change can include identifying the instantaneous increase in the plotted curvature of the optical-fiber stylet followed by the instantaneous decrease in the plotted curvature as sensed by each FBG sensor of the last three FBG sensors (e.g., the FBG sensors 426*a*, 426*b*, and 426*c*) in the distal-end portion of the optical-fiber stylet at the moment the tip of the medical device 110 is advanced into the SVC. Additionally or alternatively, the method can include automatically determining with the SVC-determiner algorithm the distinctive change in the plotted curvature of the optical-fiber stylet, or the plottable data therefor, sensed by the selection of the FBG sensors in the distal-end portion of the optical-fiber stylet at the moment the tip of the medical device 110 is advanced into the SVC.

The method can include ceasing to advance the tip of the medical device 110 through the vasculature of the patient after determining the tip of the medical device 110 is located in the SVC. The method can include confirming the tip of the medical device 110 is in the SVC by way of periodic changes in the plotted curvature of the optical-fiber stylet sensed by the selection of the FBG sensors. The periodic changes in the plotted curvature result from periodic changes in blood flow within the SVC as a heart of the patient beats.

In some alternative or additional embodiments, logic of the shape-sensing system 100 or 200 may be configured to generate a rendering of the current physical state of the stylet and, as a result, of the catheter, based on heuristics or run-time analytics. For example, the logic may be configured in accordance with machine-learning techniques to access a data store (library) with pre-stored data (e.g., images, etc.) pertaining to different regions of the stylet in which the core fibers experienced similar or identical wavelength shifts. From the pre-stored data, the current physical state of the stylet and/or the catheter may be rendered. Alternatively, as another example, the logic may be configured to determine, during run-time, changes in the physical state of each region of the stylet (and the catheter), based on at least (i) resultant wavelength shifts experienced by the core fibers, and (ii) the relationship of these wavelength shifts generated by sensors positioned along different outer core fibers at the same cross-sectional region of the stylet (or the catheter) to the wavelength shift generated by a sensor of the center core fiber at the same cross-sectional region. It is contemplated that other processes and procedures may be performed to utilize the wavelength shifts as measured by sensors along each of the core fibers to render appropriate changes in the physical state of the stylet and/or the catheter.

Notably, not one method of the shape-sensing system 100 or 200 requires an X-ray for determining whether the tip of the medical device 110 is located within the SVC of the patient. As such, patients need not be exposed to ionizing X-ray radiation when the shape-sensing system 100 or 200 is used. In addition, not one method of the shape-sensing system 100 or 200 requires an additional magnetic-sensor piece of capital equipment for determining whether the tip of the medical device 110 is located within the SVC of the patient. In addition, since, the shape-sensing system 100 or 200 does not require use of a reliable ECG P-wave like some existing systems for placing a tip of a medical device into an SVC of a patient, the shape-sensing system 100 or 200 can be used with patient having atrial fibrillation or another heart arrhythmia.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method for determining a tip of a medical device is located within a superior vena cava ("SVC"), comprising:
   advancing the tip of the medical device through a vasculature of a patient toward the SVC, the medical device including an integrated optical-fiber stylet having a plurality of fiber Bragg grating ("FBG") sensors along at least a distal-end portion of the optical-fiber stylet for shape sensing with a shape-sensing system including the medical device;
   enabling input optical signals to be sent into the optical-fiber stylet while advancing the tip of the medical device through the vasculature of the patient;
   enabling FBG sensor-reflected optical signals to be received from the optical-fiber stylet while advancing the tip of the medical device through the vasculature of the patient; and
   identifying on a display screen of the shape-sensing system a distinctive change in a plotted curvature of the optical-fiber stylet over time for a selection of the FBG sensors in the distal-end portion of the optical-fiber stylet at a moment the tip of the medical device is advanced into the SVC, thereby determining the tip of the medical device is located within the SVC.

2. The method of claim 1, further comprising enabling the FBG sensor-reflected optical signals received from the optical-fiber stylet to be algorithmically converted into a number of different plots for displaying on the display screen including the plotted curvature of the optical-fiber stylet over time.

3. The method of claim 2, wherein each plot of the number of different plots other than the plotted curvature of the optical-fiber stylet over time is selected from a plot of curvature vs. arc length, a plot of torsion vs. arc length, a plot of angle vs. arc length, and a plot of position vs. time for at least the distal-end portion of the optical-fiber stylet.

4. The method of claim 2, wherein the plotted curvature of the optical-fiber stylet over time includes a plot of curvature vs. time for each FBG sensor of the FBG sensors of the optical-fiber stylet.

5. The method of claim 1, further comprising enabling the FBG sensor-reflected optical signals received from the optical-fiber stylet to be algorithmically converted into a displayable shape for the medical device for displaying on the display screen.

6. The method of claim 1, wherein the distinctive change in the plotted curvature of the optical-fiber stylet over time is an instantaneous increase in the plotted curvature of the optical-fiber stylet over time followed by an instantaneous decrease in the plotted curvature of the optical-fiber stylet over time.

7. The method of claim 6, wherein a magnitude of the instantaneous decrease in the plotted curvature of the optical-fiber stylet over time is about twice that of the instantaneous increase in the plotted curvature of the optical-fiber stylet over time.

8. The method of claim 1, wherein the selection of the FBG sensors is a last three FBG sensors in the distal-end portion of the optical-fiber stylet.

9. The method of claim 1, further comprising:
   ceasing to advance the tip of the medical device through the vasculature of the patient after determining the tip of the medical device is located in the SVC; and
   confirming the tip of the medical device is in the SVC by way of periodic changes in the plotted curvature of the optical-fiber stylet over time for the selection of the FBG sensors, the periodic changes in the plotted curvature of the optical-fiber stylet over time resulting from periodic changes in blood flow within the SVC as a heart of the patient beats.

10. The method of claim 1, wherein advancing the tip of the medical device through the vasculature of the patient includes advancing the tip of the medical device through a right internal jugular vein, a right brachiocephalic vein, and into the SVC.

11. The method of claim 10, wherein the medical device is a central venous catheter ("CVC").

12. The method of claim 1, wherein advancing the tip of the medical device through the vasculature of the patient includes advancing the tip of the medical device through a right basilic vein, a right axillary vein, a right subclavian vein, a right brachiocephalic vein, and into the SVC.

13. The method of claim 12, wherein the medical device is a peripherally inserted central catheter (PICC).

14. A method for determining a tip of a medical device is located within a superior vena cava ("SVC"), comprising:
advancing the tip of the medical device through a vasculature of a patient toward the SVC, the medical device including an integrated optical-fiber stylet having a plurality of fiber Bragg grating ("FBG") sensors along at least a distal-end portion of the optical-fiber stylet for shape sensing with a shape-sensing system including the medical device;
enabling input optical signals to be sent into the optical-fiber stylet while advancing the tip of the medical device through the vasculature of the patient;
enabling FBG sensor-reflected optical signals to be received from the optical-fiber stylet while advancing the tip of the medical device through the vasculature of the patient;
enabling the FBG sensor-reflected optical signals received from the optical-fiber stylet to be algorithmically converted into a plot of curvature vs. time for each FBG sensor of the FBG sensors;
identifying on a display screen of the shape-sensing system an instantaneous increase in the plot of curvature vs. time for each FBG sensor of a last three FBG sensors in the distal-end portion of the optical-fiber stylet followed by an instantaneous decrease in the plot of curvature vs. time for each FBG sensor of the last three FBG sensors in the distal-end portion of the optical-fiber stylet at a moment the tip of the medical device is advanced into the SVC, thereby determining the tip of the medical device is located within the SVC; and
confirming the tip of the medical device is in the SVC by way of periodic changes in the plot of curvature vs. time for each FBG sensor of the last three FBG sensors in the distal-end portion of the optical-fiber stylet, the periodic changes in the plot of curvature vs. time for each FBG sensor of the last three FBG sensors in the distal-end portion of the optical-fiber stylet resulting from periodic changes in blood flow within the SVC as a heart of the patient beats.

15. A shape-sensing system for medical devices, comprising:
a medical device including an integrated optical-fiber stylet having a number of fiber Bragg grating ("FBG") sensors along at least a distal-end portion of the optical-fiber stylet;
an optical interrogator configured to send input optical signals into the optical-fiber stylet and receive FBG sensor-reflected optical signals from the optical-fiber stylet;
a console including memory and one or more processors configured to convert the FBG sensor-reflected optical signals from the optical-fiber stylet into plottable data by way of a number of optical signal-converter algorithms; and
a display screen configured for displaying any plot of a number of plots of the plottable data, the number of plots including at least a plot of curvature vs. time for each FBG sensor of a selection of one or more of the FBG sensors in the distal-end portion of the optical-fiber stylet for identifying a distinctive change in strain of the optical-fiber stylet at a moment a tip of the medical device is advanced into a superior vena cava ("SVC") of a patient.

16. The shape-sensing system of claim 15, further comprising an SVC-determiner algorithm configured to automatically determine the distinctive change in the strain of the optical-fiber stylet at the moment the tip of the medical device is advanced into the SVC of the patient, the distinctive change in the strain being an instantaneous increase in the strain followed by an instantaneous decrease in the strain.

17. The shape-sensing system of claim 15, wherein the SVC-determiner algorithm is configured to confirm the tip of the medical device is in the SVC by way of periodic changes in the strain of the optical-fiber stylet sensed by the selection of the FBG sensors, the periodic changes in the strain resulting from periodic changes in blood flow within the SVC as a heart of the patient beats.

18. The shape-sensing system of claim 15, further comprising an optical-fiber connector module configured to establish a first optical connection from the medical device to the optical-fiber connector module and a second optical connection from the optical-fiber connector module to the optical interrogator, the first optical connection being through a sterile drape with the medical device in a sterile field defined by the sterile drape and the optical-fiber connector module being in a non-sterile field defined by the sterile drape.

19. The shape-sensing system of claim 18, wherein the optical-fiber connector module includes one or more sensors selected from a gyroscope, an accelerometer, and a magnetometer, the one or more sensors configured to provide sensor data to the console over one or more data wires for algorithmically determining a reference plane for shape sensing with the optical-fiber stylet.

20. The shape-sensing system of claim 15, wherein the optical interrogator is an integrated optical interrogator integrated into the console.

21. The shape-sensing system of claim 15, wherein the display screen is an integrated display screen integrated into the console.

22. A medical device, comprising:
an elongated body of implementation configured to advance through a vasculature of a patient; and
an optical fiber including a cladding and one or more core fibers spatially arranged within the cladding, each of the one or more core fibers includes a plurality of sensors distributed along a longitudinal length of a corresponding core fiber and each sensor of the plurality of sensors being configured to:
(i) reflect a light signal of a different spectral width based on received incident light; and (ii) change a characteristic of the reflected light signal for use in determining a physical state of the optical fiber.

23. The medical device of claim 22, wherein the optical fiber is a multi-core optical fiber.

24. The medical device of claim 22, wherein the elongated body of implementation is one of a stylet, a catheter, and a guidewire.

25. The medical device of claim 22, further comprising an insulating layer and a conductive medium, wherein the optical fiber is encapsulated in the insulating layer and the conductive medium is encapsulated within the insulating layer.

26. The medical device of claim 22, wherein each of the plurality of sensors constitutes a reflective grating positioned at a different region of the corresponding core fiber that is distributed along the longitudinal length of the corresponding core fiber.

27. The medical device of claim 22, wherein the change in the characteristic of the reflected light signal includes a shift in wavelength applied to the reflected light signal to identify at least a type of strain.

28. The medical device of claim 27, wherein the type of strain is a compression or a tension.

29. The medical device of claim 22, further comprising a conductive medium configured to provide a pathway for electrical signals detected at a distal portion of the conductive medium.

30. The medical device of claim 22, further comprising electrical signals, wherein the electrical signals include an electrocardiogram (ECG) signal.

31. A medical device system for detecting positioning of a medical device at a target site within a vasculature of a patient, the system comprising:
the medical device comprising an optical fiber having one or more core fibers, each of the one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal for use in determining a physical state of the optical fiber; and
a console including one or more processors and a non-transitory computer-readable medium having stored thereon logic, when executed by the one or more processors, causes operations including:
providing a broadband incident light signal to the optical fiber;
receiving reflected light signals of different spectral widths of the broadband incident light signal from at least the one or more of the plurality of sensors;
processing the reflected light signals associated with the plurality of core fibers; and
determining whether the medical device is positioned at the target site of the patient based on the reflected light signals.

32. The medical device system of claim 31, wherein the optical fiber is a multi-core optical fiber.

33. The medical device system of claim 31, wherein the medical device is one of a stylet, a catheter, and a guidewire.

34. The medical device system of claim 31, wherein the target site is in one of a superior vena cava (SVC), a right atrium, and an inferior vena cava (IVC) of the vasculature of the patient.

35. The medical device system of claim 31, wherein the logic, when executed by the one or more processors, causes further operations including generating a visual representation of a physical state of at least a portion of the medical device based on characteristics of reflected light signals.

36. The medical device system of claim 35, wherein the visual representation is a three-dimensional (3D) visual representation of the physical state of at least the portion of the medical device based on the characteristics of reflected light signals.

* * * * *